United States Patent
Sullenger et al.

(10) Patent No.: US 9,061,043 B2
(45) Date of Patent: Jun. 23, 2015

(54) APTAMERS TO GLYCOPROTEIN VI

(75) Inventors: Bruce A. Sullenger, Durham, NC (US); Kristin M. Bompiani, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 13/878,539

(22) PCT Filed: Oct. 13, 2011

(86) PCT No.: PCT/US2011/001750
§ 371 (c)(1), (2), (4) Date: Apr. 9, 2013

(87) PCT Pub. No.: WO2012/050611
PCT Pub. Date: Apr. 19, 2012

(65) Prior Publication Data
US 2013/0210903 A1    Aug. 15, 2013

Related U.S. Application Data

(60) Provisional application No. 61/344,804, filed on Oct. 13, 2010.

(51) Int. Cl.
*C07H 21/02* (2006.01)
*C07H 21/04* (2006.01)
*A61K 48/00* (2006.01)
*A61K 31/7105* (2006.01)
*C12N 15/115* (2010.01)

(52) U.S. Cl.
CPC .......... *A61K 31/7105* (2013.01); *C12N 15/115* (2013.01); *C12N 2310/16* (2013.01)

(58) Field of Classification Search
CPC .............................. A61K 48/00; C12N 15/111
See application file for complete search history.

(56) References Cited

U.S. PATENT DOCUMENTS

| | | |
|---|---|---|
| 2006/0264369 A1 | 11/2006 | Diener et al. |
| 2008/0220055 A1 | 9/2008 | Ludwig et al. |
| 2010/0003244 A1* | 1/2010 | Munch et al. ............... 424/133.1 |
| 2010/0184822 A1 | 7/2010 | Sullenger et al. |
| 2010/0311820 A1* | 12/2010 | Layzer et al. ............... 514/44 R |

OTHER PUBLICATIONS

International Search Report for PCT/US2011/001750 mailed Aug. 3, 2012.
T.L. Kiefer et al., "Inhibitors of Platelet Adhesion" Circulation, Dec. 15, 2009, vol. 120, pp. 2488-2495.
M. Li et al., "Selecting Aptamers for a Glycoprotein Through the Incorporation of the Boronic Acid Moiety", J. Am. Chem. Soc., Sep. 24, 2008, vol. 130, No. 38, pp. 12636-12638 (Author Manuscript).

* cited by examiner

*Primary Examiner* — Amy Bowman
(74) *Attorney, Agent, or Firm* — Andrus Intellectual Property Law, LLP

(57) ABSTRACT

The present invention relates, in general, to glycoprotein VI (GPVI) and, in particular, to aptamers to GPVI and to compositions comprising same. The invention also relates to methods of inhibiting platelet aggregation using an aptamer that binds to and inhibits the activity of GPVI. The invention further relates to antidotes to GPVI aptamers and to methods of using such antidotes to reverse aptamer-induced platelet inhibition. The invention also relates to aptamers that bind to and enhance the activity of GPVI.

16 Claims, 18 Drawing Sheets

Nitrocellulose binding of selected GPVI aptamers.

Figure 1D

GPVI aptamers isolated:

| Clone | RNA Sequences (Where C's and U's are 2'Flouro-ribonucleotides) | Kd (nM) |
|---|---|---|
| cR9-37 | GGGGAGGAGGACGAUGCGGACAGUGUCGACAGUGUCACACUUUGCGUAAGCCGCUAGCCCCUCCGCAGAGACUCGCUGAGGAUCCGAGA | 160 |
| cR9-40 | GGGAGGAGGACGAUGCGGCGAGUGUAAGCAUCACUGCAUCUAGCGUAAGCCACCCAAACAGACGACUCGCUGAGGAUCCGAGA | 60 |
| cR9-44 | GGGAGGAGGACGAUGCGGCAUCAGAGACUGCAUCCAGCAUAAGCCACCACCAGAGACCGUCAGACGACUCGCUGAGGAUCCGAGA | 21 |
| cR9-45 | GGGAGGAACGAUGCGGGUGACGUGACGACGGACGCGACAGCCCAGCAUAAGCCACGUGUGACAGACGACUCGCUGAGGAUCCGAGA | 25 |
| cR9-46 | GGGAGGAGGACGAUGCGGGACGCGGCCACCCAAAACAGGGCUCACGUCUGGCAU AAGCCUGCCACCAGACGACUCGCUGAGGAUCCGAGA | 55 |
| cR10-75 | GGGAGGAGGACGAUGCGGACGGCCAAACGCCUAGCAUAAGCCCAUCAG UCACUCCCACCAGACGACUCGCUGAGGAUCCGAGA | 35 |
| cR10-76 | GGGAGGAGGACGAUGCGGGUGACGGGACGCGGACAGCCCAGCAUAAGCCACGUGUGACAGACGACUCGCUGAGGAUCCGAGA | 33 |
| cR13-4 | GGGAGGAGGACGAUGCGGGUGACGGGACGCGGACAGCCCAGCAUAAGCCACGUGUGACAGACGACUCGCUGAGGAUCCGAGA | 34 |

Platelet aggregometry with aptamer cR13-4.

Sel3 Library control

GPVI aptamer cR13-4

Figure 4

GPVI aptamer data

High affinity pools of RNA were generated against human GPVI via SELEX (nitrocellulose filter binding assays)

Individual RNA sequences that bind to GPVI (Note the cloned DNA sequences are shown, but the functional sequences are RNA)

Round 9 clones:

Round 10 clones:

Round 12 (and 13) clones:

Aptamer cR13-4

Aptamer cR13-4 binds soluble GPVI with high affinity; all aptamers bind similar sites on GPVI (nitrocellulose filter binding)

cR13-4 binds to human platelets with high affinity (flow cytometry)

cR13-4 does not bind to with mouse platelets (flow cytometry)

cR13-4 prolongs a platelet function analyzer 100 (PFA-100) assay

| Compound | PFA-100 Closing Time | |
|---|---|---|
| | ADP/Collagen | Epi./Collagen |
| Buffer | 126 | 182 |
| Sel2 (1 uM) | 157 | 234 |
| cR13-4 (1 uM) | 216 | 299 | cR13-4 stimulates platelet aggregation (light transmission aggregometry assays)

cR13-4 may spontaneously multimerize and form higher order structures (native gel electrophoresis)

Aptamer cR13-4 has been shortened to 43 nucleotides; a mutant control aptamer was designed An oligonucleotide antidote can reverse soluble GPVI/aptamer binding, but cannot reverse platelet activation by the aptamer

Figure 5

RNA sequences that bind to human GPVI

Round 9

| | |
|---|---|
| CR9-31 | GGGGAGGAUGCUGCCGGGAGUCCUAGCAUAAGCCCAUGCGUACACCCCGGUCAGACGACACUCGCUGAGGAUCCGAGA |
| CR9-34 | GGAAGGACGAUGCGGACGGCGGACGCUGACGGUGCCAGCAUAGCCGCCAUCGAAUCCACGAGACGACUCGCUGAGGAUCCGAGA |
| CR9-36 | GGGAGGACGAUGCGGACGGCUUCGACAGUGACGAUGUACCAAAGCUAGCGUAAGCCCUCCCGUCAGACGACUCGCUGAGGAUCCGAGA |
| CR9-37 | GGGAGGACGAUGCGGACAGUGACAGUGUACAACAGGUCAAAGCCUUUGCGUAAGCCGUAAGCCGCUAAGCCCUCCGAAGCUCGCUGAGGAUCCGAGA |
| CR9-38 | GGGAGGACGAUGCGGAUGGCGGAUACACAUCGCGCACGCUACGGCUAUAAUAUACCGCGUUGCAUAAGCCACCCAGACGACGACUCGCUGAGGAUCCGAGA |
| CR9-39 | GGGAGGACGAUGCGGACGGCGGAAUGGCGCGAAAGCCAUCAGAGCCAUCAGAGCCAAAUCUGCACGCAGCAUCGAGACGACGACUCGCUGAGGAUCCGAGA |
| CR9-40 | GGGAGGACGAUGCGGACGGCGGACGGCAAACGCUGACAAAACGCUGACACUAGCUGACCCUAGCCAGACAGACGACUCGCUGAGGAUCCGAGA |
| CR9-41 | GGGAGGACGAUGCGGACGGCGGCGGACAGAGCUGACGUGCAAAUCUAGCAUGUGCACAUCAGACGCACGACGACUCGCUGAGGAUCCGAGA |
| CR9-42 | GGGAGGACGAUGCGGACGGCGGCGGCCAACACUGCGGUGCAAUAACUGCUGACGCAUAGCCGUAAGCCGUAAGCGACGACGACUCGCUGAGGAUCCGAGA |
| CR9-43 | GGGAGGACGAUGCGGACGGCGGCGGACCAAUUCGGCAUCCAGCAAGCCAUCCAGCCAUCAGCCGCAUAAGCCACCAGAGACGACGACUCGCUGAGGAUCCGAGA |
| CR9-44 | GGGAGGACGAUGCGGACGGCGGGCGGGGCGGGCAACAGGCGACGUGACGUGACGUGACGAGCUUCAGCAGACCCAGAGACCACGUGAGACGACUCGCUGAGGAUCCGAGA |
| CR9-45 | GGGAGGAACGAUGCGGAGCGAGCGACUGGACGCCAACAGGGCGACGCCACUCCAGACCCAUAAGCCGUAGACAGACAGACAGACGACUCGCUGAGGAUCCGAGA |
| CR9-46 | GGGAGGACGAUGCGGACGGCGGCCAAGACUUCCCUAGCAGCCACGUGACAUAAGCCCUGCCACGCGUCAGACUGCCCACUGCGACAGACGACUCGCUGAGGAUCCGAGA |
| CR9-47 | GGGAGGACGAUGCGGACGGCGGGGCAAGACUUCUCCCCGCUAGCAGCACCGACGCACGUCCUGUCAUAAGCCUGCCUCCAGACGACUCGCUGAGGAUCCGAGA |
| CR9-48 | GGGAGGACGAUGCGGACGGCGGGGCGCUCUGGACGCAGCUACGGCUAUCAGCUGCAUAAGCCGAACUGGGCAUAAGCCACACCACACGACGACUCGCUGAGGAUCCGAGA |
| CR9-52 | GGGAGGACGAUGCGGACGGCGGGCGUCUGGAACGCUGACAUAAGCCCAUAUCAGCAGCAUCAAGCCUACCAACCCUACACGCAGCAGACGACGACUCGCUGAGGAUCCGAGA |
| CR9-53 | GGGAGGACGAUGCGGACGGCGGGCGGUCUGGACGCAGCAACCUUGACAUCCAGCAUAAGCCCACGCGCAGACUAAGACAGCAGACGACGACUCGCUGAGGAUCCGAGA |
| CR9-54 | GGGAGGACGAUGCGGACGGCGGACUGACGGAGGGCCAAUACGCAUAAGCCUACCUGACUGACUACUCGAGACACCAAGAACAGACAGACAGCGACGACUCGCUGAGGAUCCGAGA |
| CR9-55 | GGGAGGACGAUGCGGACGGCGGACGGCGGCGGACGCAAUUCGCGUCAGCGCACGCGUAAGCCUGUCAAAUCUGCUAGCAGACAGACAGACAGACGACUCGCUGAGGAUCCGAGA |
| CR9-56 | GGGAGGACGAUGCGGACGGCGGGUUGUGUUAACGGACAGUGACGUGUCCACGACACACCCGUCGCGUCAAGACGACUCGCUGAGGAUCCGAGA |
| CR9-57 | GGGAGGACGAUGCGGACGGCGGACAGUGUAACGGACAGUGGUCACACAUCGGACACUGGGCAAGCGCACUGACAUUUGCGUAAGCCGCUAGACAGACGACUCGCUGAGGAUCCGAGA |
| CR9-58 | GGGAGGACGAUGCGGACGGCGGAUCACAUCGGACACUGGGCAAGCCAUAUAGCGCACUGCCUAAGCCGCCAGCGUAGCAGACAGACUCGCUGAGGAUCCGAGA |
| CR9-59 | GGGAGGACGAUGCGGACGGCGGGGACGCGGAUGGGACGGUCCACAGGACGACGAACAAGCCUAGCACGUGUGACACCAGAGACUCGCUGAGGAUCCGAGA |
| CR9-60 | AGGGAGGACGAUGCGGACGGCGGGGACGCGGUCCACGGCGACGAACUAAGCGUCUAGCCGUAAGCGUAAGCCUAGACGACGAGACUCGCUGAGGAUCCGAGA |

Round 10

| | |
|---|---|
| CR10-62 | GGGAGGACGACGCGGUCCACCGGACGCCAUCCAGCGACGAUCAGCCAUAAAGCGUCAGCCUAGCCGUACCACGAGACGAGCGACUCGCUGAGGAUCCGAGA |
| CR10-64 | GGGAGGACGACGCGGGUACGCGGUCGUACGGCCAUCGCCUAGCCAUCAGCCAUAAAAGCGUCAGCCAUAGCCUACCAGCAGACCUCCAGCAGACCUAGACGACUCGCUGAGGAUCCGAGA |
| CR10-66 | GGGAGGACGACGCGGGCAACGGCUAGAGCGCCAUGCAACACGCCCUAAGCCAUAAAGCGCCCAAAAACCGCCAAAAACCACCAGUAAGACCAGACAGACUCGCUGAGGAUCCGAGA |
| CR10-67 | GGGAGGACGACGCGGGCGAUGCCAGCCAUAAAGCGCAUCAAUUCGCCCCCAGACCGACAGACAGACAGACUCGCUGAGGAUCCGAGA |
| CR10-69 | GGGAGGACGACGCGGGCCACUGACGGGUACGGCUAUCAGCAUAUAAGCCCUUAAAACGCUCUUCAGACGACAGACAGACUCGCUGAGGAUCCGAGA |
| CR10-71 | GGGAGGACGACGCGGGCCACUGACGGCCCACUGACAGGCUUAAUCGCGCAUAUAAGCCAACACGCUCUUCCACACAGCAGACAACAGACUCGCUGAGGAUCCGAGA |
| CR10-72 | GGGAGGACGACGCGGGUCCUUACGGGGCUACAGCAGCCUUAGACGCCCUUACACACGCCCUUCCACACCGAGACGCGGACUCGCUGAGGAUCCGAGA |
| CR10-73 | GGGAGGACGACGCGGGUCUAACGCGGUACGCAACGCCAAACAGCCCUAAAGCGUCAAAACGCCCUUAAGCGCGUCCAGCACACAGCGACUCGCUGAGGAUCCGAGA |
| CR10-75 | GGGAGGACGACGCGGGCUUACGGGCAUGCCAUCCUAAGCCGCCAUAAGCGUCUCCCCAAACCCGUACUCAAACCGCCAAUCCGAGACAGACGACUCGCUGAGGAUCCGAGA |
| CR10-76 | GGGAGGACGACGCGGGUCUAAACCGGGUACUGGGUACUCCGACUAAGCCAUAAAGCCCAGAGAAUCCCACAGGCGUUGACUUCGCUGAGACGACUCGCUGAGGAUCCGAGA |
| CR10-79 | GGGAGGACGACGCGGGCUUAACGGGUACUGGCUAAUCCGAGAUAAGCCAUAAAGCCCAGACCCCACAGUCGACCCUGCCACAGACAGACGACUCGCUGAGGAUCCGAGA |
| CR10-81 | GGGAGGACGACGCGGGACCUAAUCCGGGACCCUUAGCCACUCCGCCAUCAAAAACCGCAUAAUAACACAGACACGACAAGACGCUGAGGAUCCGAGA |
| CR10-82 | GGGAGGACGACGCGGGACUGAACGCGCGUCAACUGGCAUCAGCCAUAGCCUUCCAACAGCAGCCUUCCAACGGGCUCAGCCUACAACAGACAGCAGACUCGCUGAGGAUCCGAGA |
| CR10-84 | GGGAGGACGACGCGGGCUCUGAACGGCUAUAACUUGCCACUCCAUCCAGGGCCAUCAUGCCACAUCACAUACAAACACAGAGACAGACAGACUCGCUGAGGAUCCGAGA |
| CR10-86 | GGGAGGACGACGCGGGUCGUGACGGCGGCUCAGCCAUAUAACUCGCCAUCAUCAACUCAACGGGCGUAGCCUAACACAGACGCGUGCUGAGACAGACGACUCGCUGAGGAUCCGAGA |
| CR10-87 | GGGAGGACGACGCGGGUCGGGAACGGCGGCCCAAGGCCAUAUCGGCAUGACCUUCCAACAACUCCAACAACUCCUCGCAAUUCAGACAGACGACUCGCUGAGGAUCCGAGA |
| CR10-89 | GGGAGGACGACGCGGAUGCCCCAAAGCCCAUCAACGCGUCAGCCAUAGCCGACCAAUUCAGACAUCAGACAAUUCAGACACGCUAGACGACGACUCGCUGAGGAUCCGAGA |

Round 12

| | |
|---|---|
| cR12-31 | GGGAGGACGACGCGGGUGACGUGACGCGUAGCCAGCGCCCAGCAUAAGCCACGUGACAGACGACUCGCUGAGGAUCCGAGA |
| cR12-32 | GGGAGGACGACGCGGGUGACGUGACGCGUGAGCCAGCGCCCAGCAUAAGCCACCCGUGUGACAGACGACUCGCUGAGGAUCCGAGA |

Round 13

| | |
|---|---|
| cR13-1 | GGGAGGACGACGCGGGUGACGCGGACCGAGCGCCGACUUCAGCGACGAUAUGACCAGCAGCCAGUGCGACACUGCGACACUGCCAGACUCGCUGAGGAUCCGAGA |
| cR13-4 | GGGAGGACGACGCGGGUGACGCGGUGACCGACGGGUGACCGACGAGCGCCGACAGCCAGCGCCGACAGCCGCCCAGCAUAUGACCAGCAUAUGCCCGUGACACUGCGCCUGACACUGCGCUGCUGAGGAUCCGAGA |

SEQUENCE LISTING

```
<160> NUMBER OF SEQ ID NOS: 117

<210> SEQ ID NO 1
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggggaggau gcugccggga guccuagcau aagcccaugc guacaccccc gggucagacg      60
acucgcugag gauccgaga                                                   79

<210> SEQ ID NO 2
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gggaagacga ugcggacggc gauaaggugc ccagcaucag ccgcaucgaa ucccacagac      60
gacucgcuga ggauccgaga                                                  80

<210> SEQ ID NO 3
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gggaggacga ugcggcucga cguaaaccaa agcucaucua gcguaagccu cccgucagac      60
gacucgcuga ggauccgaga                                                  80

<210> SEQ ID NO 4
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggggaggacg augcggacag ugucacacac uuugcguaag ccgcuagccc ccuccgcaga      60
cgacucgcug aggauccgag a                                                81
```

```
<210> SEQ ID NO 5
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggaggacga ugcggugaua caucgcgucu ggcauaagcc uaccgcuccg aagcucagac    60
gacucgcuga ggauccgaga                                                80

<210> SEQ ID NO 6
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gggaggacga ugcggaaugg caucacgccu auaauauacc cgcguugcau accccagacg    60
acucgcugag gauccgaga                                                 79

<210> SEQ ID NO 7
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gggaggacga ugcggcgagu guaagcauca cugcaucuag cguaagccac ccaaacagac    60
gacucgcuga ggauccgaga                                                80

<210> SEQ ID NO 8
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gggaggacga ugcggcaaac gcugacaucc agcauaagcc ucccugcacg gacaucagac    60
gacucgcuga ggauccgaga                                                80

<210> SEQ ID NO 9
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gggaggacga ugcggcgagu guaagcauca cugcaucuag cguaagcccc caaacagacg    60
acucgcugag gauccgaga                                                 79

<210> SEQ ID NO 10
<211> LENGTH: 80
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 10
gggaggacga ugcggccaac uaaucgggca agcauccagc auaagccccc cacaucagac    60
gacucgcuga ggauccgaga                                                80

<210> SEQ ID NO 11
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gggaggacga ugcggcauca gacugcaucc agcauaagcc accaccagag accgucagac    60
gacucgcuga ggauccgaga                                                80

<210> SEQ ID NO 12
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gggaggaacg augcggguga cguggacggc gacagcccag cauaagccac gugugacaga    60
cgacucgcug aggauccgag a                                              81

<210> SEQ ID NO 13
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gggaggacga ugcgggcacc caaaacaggg gcucacgucu ggcauaagcc ugcccacaga    60
cgacucgcug aggauccgag a                                              81

<210> SEQ ID NO 14
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gggaggacga ugcggggcaa guacuucucc cucauccagc auaacccgcc cacugcagac    60
gacucgcuga ggauccgaga                                                80

<210> SEQ ID NO 15
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 15
gggaggacga ugcggggcag cauacugccc uucgucuugc auaagccucc gucaccagac    60
gacucgcuga ggauccgaga                                                80

<210> SEQ ID NO 16
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gggaggacga ugcgguccug gacggcacua cgccuugcau aagccaagac ugcaccagac    60
gacucgcuga ggauccgaga                                                80

<210> SEQ ID NO 17
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gggaggacga ugcggucauc gaacggcugc auccagcaua aaccaacccc acgcgcagac    60
gacucgcuga ggauccgaga                                                80

<210> SEQ ID NO 18
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gggaggacga ugcggaggcc acuaccucau gcauccagca uaagccuacc gagaacagac    60
gacucgcuga ggauccgaga                                                80

<210> SEQ ID NO 19
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gggaggacga ugcggacggg aaaccuugca ucagccgcau aauccguaca ccaugcagac    60
gacucgcuga ggauccgaga                                                80

<210> SEQ ID NO 20
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gggaggacga ugcggcaaua ccgcguccag cguaagccuu caacaacucg ggcucaaaca    60
```

```
acucgcugag gauccgaga                                                  79
```

<210> SEQ ID NO 21
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21

```
gggaggacga ugcgguugug uaacggcacu acugcuugca uaauaccccu cugcaccaga    60
cgacucgcug aggauccgag a                                              81
```

<210> SEQ ID NO 22
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22

```
gggaggacga ugcggacagu gucacacacu uugcguaagc cgcuagcccc cuccgcagac    60
gacucgcuga ggauccgaga                                                80
```

<210> SEQ ID NO 23
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23

```
gggaggacga ugcggccacu aaucgggcaa gcauccagca uaagcccccc acaucagacg    60
acucgcugag gauccgaga                                                 79
```

<210> SEQ ID NO 24
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24

```
agggaggacg augcggguga cguggacggc gacagcccag cauaagccac gugugacaga    60
cgacucgcug aggauccgag a                                              81
```

<210> SEQ ID NO 25
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25

```
gggaggacga ugcgguccac gguggacga cgaacuaacg ucuagcguaa gcccacagac    60
gacucgcuga ggauccgaga                                                80
```

<210> SEQ ID NO 26

-continued

```
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gggaggacga ugcgguacca cagcgcaucc agcauaagcc uccaccgcgg ucagacgacu      60
cgcugaggau ccgaga                                                     76

<210> SEQ ID NO 27
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gggaggacga ugcggacggc caaacgccua gcauaagccc aucagucacu cccaccagac      60
gacucgcuga ggauccgaga                                                 80

<210> SEQ ID NO 28
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gggaggacga ugcggacggg cagugagcua ucacgcccua acguaagccg cauugcagac      60
gacucgcuga ggauccgaga                                                 80

<210> SEQ ID NO 29
<211> LENGTH: 83
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gggaggacga ugcggucacu gacgggccau uagcaucugg cauaagccuc cacugcagca      60
gacgacucgc ugaggauccg aga                                             83

<210> SEQ ID NO 30
<211> LENGTH: 81
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gggaggacga ugcgggugac guggacggcg acagcccagc auaagccacg ugugacaaga      60
cgacucgcug aggauccgag a                                               81

<210> SEQ ID NO 31
<211> LENGTH: 80
<212> TYPE: RNA
<213> ORGANISM: Artificial Sequence
<220> FEATURE:
```

<223> OTHER INFORMATION: Description of Artificial Sequence: Synthetic
     oligonucleotide

<400> SEQUENCE: 31
gggaggacga ugcggacggc uucagcccag cauaagccgc uuacuccccc ccggacagac    60
gacucgcuga ggauccgaga                                               80

<210> SEQ ID NO 32
<211> LENGTH: 81
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 32
gggaggacga ugcggccaac agcaaaccgu gucuagcaua agccucucaa cacgcgcaga    60
cgacucgcug aggauccgag a                                             81

<210> SEQ ID NO 33
<211> LENGTH: 80
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 33
gggaggacga ugcggacggc caaacgccua gcauaagccc aucagucacu cccaccagac    60
gacucgcuga ggauccgaga                                               80

<210> SEQ ID NO 34
<211> LENGTH: 80
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 34
gggaggacga ugcgggugac guggacggcg acagcccagc auaagccacg ugugacagac    60
gacucgcuga ggauccgaga                                               80

<210> SEQ ID NO 35
<211> LENGTH: 80
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 35
gggaggacga ugcggacugg gacgaccaug gcauaaaccg cagacccgcc cuccucagac    60
gacucgcuga ggauccgaga                                               80

<210> SEQ ID NO 36
<211> LENGTH: 81
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 36

```
gggaggacga ugcggccaac uaaucgggac aagcauccag cauaagcccc ccacaucaga    60
cgacucgcug aggauccgag a                                             81
```

<210> SEQ ID NO 37
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37

```
gggaggacga ugcggccuua caauccgcgu ccagcauaag ccugccaaac agcgccagac    60
gacucgcuga ggauccgaga                                               80
```

<210> SEQ ID NO 38
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38

```
gggaggacga ugcggacggg aaaccuugca ucagccgcau aauccguaca ccaugcagac    60
gacucgcuga ggauccgaga                                               80
```

<210> SEQ ID NO 39
<211> LENGTH: 78
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39

```
gggaggacga ugcggcucgg agugccacua cgggcauagc auaagcugaa cagcagacga    60
cucgcugagg auccgaga                                                 78
```

<210> SEQ ID NO 40
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40

```
gggaggacga ugcggcaaua ccgcguccag cguaagccuu ccaacaacuc gggcucagac    60
gacucgcuga ggauccgaga                                               80
```

<210> SEQ ID NO 41
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41

```
gggaggacga ugcggcccca aagccacauc uggcaucagc cgacccaacg acauucagac    60
gacucgcuga ggauccgaga                                               80
```

<210> SEQ ID NO 42
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gggaggacga ugcgggugac guggacggcg acagcccagc auaagccacg ugugacagac    60
gacucgcuga ggauccgaga                                                80

<210> SEQ ID NO 43
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
gggaggacga ugcgggugac guggacggcg acagcccagc auaagcccgu gugacagacg    60
acucgcugag gauccgaga                                                 79

<210> SEQ ID NO 44
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gggaggacga ugcggcgagc cggacuucag ccagugauau gaugcgacac acugccagac    60
gacucgcuga ggauccgaga                                                80

<210> SEQ ID NO 45
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gggaggacga ugcgggugac guggacggcg acagcccagc auaagccacg ugugacagac    60
gacucgcuga ggauccgaga                                                80

<210> SEQ ID NO 46
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gggggaggat gctgccggga gtcctagcat aagcccatgc gtaccccccc gggtcagacg    60
actcgctga                                                            69

<210> SEQ ID NO 47
<211> LENGTH: 70

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gggaagacga tgcggacggc gataaggtgc ccagcatcag ccgcatcgaa tcccacagac      60
gactcgctga                                                            70

<210> SEQ ID NO 48
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gggaggacga tgcggctcga cgtaaaccaa agctcatcta gcgtaagcct cccgtcagac      60
gactcgctga                                                            70

<210> SEQ ID NO 49
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggggaggacg atgcggacag tgtcacacac tttgcgtaag ccgctagccc cctccgcaga      60
cgactcgctg a                                                          71

<210> SEQ ID NO 50
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gggaggacga tgcggtgata catcgcgtct ggcataagcc taccgctccg aagctcagac      60
gactcgctga                                                            70

<210> SEQ ID NO 51
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gggaggacga tgcggaatgg catcacgcct ataatatacc cgcgttgcat accccagacg      60
actcgctga                                                             69

<210> SEQ ID NO 52
<211> LENGTH: 70
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 52
gggaggacga tgcggcgagt gtaagcatca ctgcatctag cgtaagccac ccaaacagac    60
gactcgctga                                                          70

<210> SEQ ID NO 53
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gggaggacga tgcggcaaac gctgacatcc agcataagcc tccctgcacg gacatcagac    60
gactcgctga                                                          70

<210> SEQ ID NO 54
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gggaggacga tgcggcgagt gtaagcatca ctgcatctag cgtaagcccc caaacagacg    60
actcgctga                                                           69

<210> SEQ ID NO 55
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gggaggacga tgcggccaac taatcgggca agcatccagc ataagccccc cacatcagac    60
gactcgctga                                                          70

<210> SEQ ID NO 56
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gggaggacga tgcggcatca gactgcatcc agcataagcc accaccagag accgtcagac    60
gactcgctga                                                          70

<210> SEQ ID NO 57
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

```
gggaggaacg atgcgggtga cgtggacggc gacagcccag cataagccac gtgtgacaga    60
cgactcgctg a                                                          71

<210> SEQ ID NO 58
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gggaggacga tgcgggcacc caaaacaggg gctcacgtct ggcataagcc tgcccacaga    60
cgactcgctg a                                                          71

<210> SEQ ID NO 59
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gggaggacga tgcggggcaa gtacttctcc ctcatccagc ataacccgcc cactgcagac    60
gactcgctga                                                            70

<210> SEQ ID NO 60
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gggaggacga tgcggggcag catactgccc ttcgtcttgc ataagcctcc gtcaccagac    60
gactcgctga                                                            70

<210> SEQ ID NO 61
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gggaggacga tgcggtcctg gacggcacta cgccttgcat aagccaagac tgcaccagac    60
gactcgctga                                                            70

<210> SEQ ID NO 62
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gggaggacga tgcggtcatc gaacggctgc atccagcata aaccaacccc acgcgcagac    60
gactcgctga                                                            70
```

<210> SEQ ID NO 63
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gggaggacga tgcggaggcc actacctcat gcatccagca taagcctacc gagaacagac    60
gactcgctga                                                            70

<210> SEQ ID NO 64
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gggaggacga tgcggacggg aaaccttgca tcagccgcat aatccgtaca ccatgcagac    60
gactcgctga                                                            70

<210> SEQ ID NO 65
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gggaggacga tgcggcaata ccgcgtccag cgtaagcctt caacaactcg ggctcaaaca    60
actcgctga                                                             69

<210> SEQ ID NO 66
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gggaggacga tgcggttgtg taacggcact actgcttgca taatacccct ctgcaccaga    60
cgactcgctg a                                                          71

<210> SEQ ID NO 67
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gggaggacga tgcggacagt gtcacacact ttgcgtaagc cgctagcccc ctccgcagac    60
gactcgctga                                                            70

<210> SEQ ID NO 68
<211> LENGTH: 69
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 68
gggaggacga tgcggccact aatcgggcaa gcatccagca taagcccccc acatcagacg    60
actcgctga                                                            69

<210> SEQ ID NO 69
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
agggaggacg atgcgggtga cgtggacggc gacagcccag cataagccac gtgtgacaga    60
cgactcgctg a                                                         71

<210> SEQ ID NO 70
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gggaggacga tgcggtccac ggtgggacga cgaactaacg tctagcgtaa gcccacagac    60
gactcgctga                                                           70

<210> SEQ ID NO 71
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gggaggacga tgcggtacca cagcgcatcc agcataagcc tccaccgcgg tcagacgact    60
cgctga                                                               66

<210> SEQ ID NO 72
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gggaggacga tgcggacggc caaacgccta gcataagccc atcagtcact cccaccagac    60
gactcgctga                                                           70

<210> SEQ ID NO 73
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 73
gggaggacga tgcggacggg cagtgagcta tcacgccta acgtaagccg cattgcagac    60
gactcgctga    70

<210> SEQ ID NO 74
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gggaggacga tgcggtcact gacgggccat tagcatctgg cataagcctc cactgcagca    60
gacgactcgc tga    73

<210> SEQ ID NO 75
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gggaggacga tgcgggtgac gtggacggcg acagcccagc ataagccacg tgtgacaaga    60
cgactcgctg a    71

<210> SEQ ID NO 76
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gggaggacga tgcggacggc ttcagcccag cataagccgc ttactccccc ccggacagac    60
gactcgctga    70

<210> SEQ ID NO 77
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gggaggacga tgcggccaac agcaaaccgt gtctagcata agcctctcaa cacgcgcaga    60
cgactcgctg a    71

<210> SEQ ID NO 78
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gggaggacga tgcggacggc caaacgccta gcataagccc atcagtcact cccaccagac    60

```
gactcgctga                                                            70

<210> SEQ ID NO 79
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79 ggggaggacga tgcgggtgac gtggacggcg acagcccagc ataagccacg tgtgacagac    60
gactcgctga                                                            70

<210> SEQ ID NO 80
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80 ggggaggacga tgcggactgg gacgaccatg gcataaaccg cagacccgcc ctcctcagac    60
gactcgctga                                                            70

<210> SEQ ID NO 81
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81 ggggaggacga tgcggccaac taatcgggac aagcatccag cataagcccc ccacatcaga    60
cgactcgctg a                                                          71

<210> SEQ ID NO 82
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82 ggggaggacga tgcggcctta caatccgcgt ccagcataag cctgccaaac agcgccagac    60
gactcgctga                                                            70

<210> SEQ ID NO 83
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83 ggggaggacga tgcggacggg aaaccttgca tcagccgcat aatccgtaca ccatgcagac    60
gactcgctga                                                            70
```

```
<210> SEQ ID NO 84
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gggaggacga tgcggctcgg agtgccacta cgggcatagc ataagctgaa cagcagacga        60
ctcgctga                                                                68

<210> SEQ ID NO 85
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gggaggacga tgcggcaata ccgcgtccag cgtaagcctt ccaacaactc gggctcagac        60
gactcgctga                                                              70

<210> SEQ ID NO 86
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gggaggacga tgcggcccca aagccacatc tggcatcagc cgacccaacg acattcagac        60
gactcgctga                                                              70

<210> SEQ ID NO 87
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gggaggacga tgcgggtgac gtggacggcg acagcccagc ataagccacg tgtgacagac        60
gactcgctga                                                              70

<210> SEQ ID NO 88
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gggaggacga tgcgggtgac gtggacggcg acagcccagc ataagcccgt gtgacagacg        60
actcgctga                                                               69

<210> SEQ ID NO 89
<211> LENGTH: 70
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 89
gggaggacga tgcgggtgac gtggacggcg acagcccagc ataagccacg tgtgacagac    60
gactcgctga                                                            70

<210> SEQ ID NO 90
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gggaggacga tgcgggtgac gtggacggcg acagcccagc ataagccacg tgtgacagac    60
gactcgctga                                                            70

<210> SEQ ID NO 91
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gggaggacga tgcgggtgac gtggacggcg acagcccagc ataagccacg tgtgacagac    60
gactcgctga                                                            70

<210> SEQ ID NO 92
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gggaggacga tgcgggtgac gtggacggcg acagcccagc ataagccacg tgtgacagac    60
gactcgctga                                                            70

<210> SEQ ID NO 93
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gggaggacga tgcgggagag ctgtacgcct agcatcagcc tgcgctgcgt acgacagacg    60
actcgctga                                                             69

<210> SEQ ID NO 94
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 94
gggaggacga tgcgggtgac gtggacggcg acagcccagc ataagcccgt gtgacagacg    60
actcgctga                                                           69

<210> SEQ ID NO 95
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gggaggacga tgcgggtgac gtggacggcg acagcccagc ataagccacg tgtgactgac    60
gactcgctga                                                          70

<210> SEQ ID NO 96
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gggaggacga tgcgggtgac gtggacggcg acagcccagc ataagccacg tgtgacagac    60
gactcgctga                                                          70

<210> SEQ ID NO 97
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gggaggacga tgcgggtgac gtggacggcg acagcccagc ataagcccgt gtgacagacg    60
actcgctga                                                           69

<210> SEQ ID NO 98
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gggaggacga tgcgggtgac gtggacggcg acagcccagc ataagccacg tgtgacagac    60
gactcgctga                                                          70

<210> SEQ ID NO 99
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gggaggacga tgcgggtgac gtggacggcg acagcccagc ataagccacg tgtgacagac    60
```

-continued

```
gactcgctga                                                              70

<210> SEQ ID NO 100
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gggaggacga tgcgggtgac gtggacggcg acagcccagc ataagcccgt gtgacagacg        60
actcgctga                                                               69

<210> SEQ ID NO 101
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gggaggacga tgcgggtgac gtggacggcg acagcccagc ataagccacg tgtgacagac        60
gactcgctga                                                              70

<210> SEQ ID NO 102
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gggaggacga tgcgggtgac gtggacggcg acagcccagc ataagccacg tgtgacagac        60
gactcgctga                                                              70

<210> SEQ ID NO 103
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gggaggacga tgcgggtgac gtggacggcg acagcccagc ataagccacg tgtgacagac        60
gactcgctga                                                              70

<210> SEQ ID NO 104
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gggaggacga tgcgggtgac gtggacggcg acagcccagc ataagccacg tgtgacagac        60
gactcgctga                                                              70

<210> SEQ ID NO 105
```

-continued

```
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gggaggacga tgcgggtgac gtggacggcg acagcccagc ataagccacg tgtgacagac      60
gactcgctga                                                              70

<210> SEQ ID NO 106
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gggaggacga tgcgggtgac gtggacggcg acagcccagc ataagcccgt gtgacagacg      60
actcgctga                                                               69

<210> SEQ ID NO 107
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gggaggacga tgcgggtgac gtggacggcg acagcccagc ataagccacg tgtgacagac      60
gactcgctga                                                              70

<210> SEQ ID NO 108
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gggaggacga tgcgggtgac gtggacggcg acagcccagc ataagccacg tgtgacagac      60
gactcgctga                                                              70

<210> SEQ ID NO 109
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gggaggacga tgcgggtgac gtggacggcg acagcccagc ataagccacg tgtgacagac      60
gactcgctga                                                              70

<210> SEQ ID NO 110
<211> LENGTH: 69
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 110
gggaggacga tgcgggtgac gtggacggcg acagcccagc ataagcccgt gtgacagacg    60
actcgctga                                                            69

<210> SEQ ID NO 111
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gggaggacga tgcgggtgac gtggacggcg acagcccagc ataagccacg tgtgacagac    60
gactcgctga                                                           70

<210> SEQ ID NO 112
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gggaggacga tgcgggtgac gtggacggcg acagcccagc ataagccacg tgtgacagac    60
gactcgctga                                                           70

<210> SEQ ID NO 113
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gggaggacga tgcgggtgac gtggacggcg acagcccagc ataagcccgt gtgacagacg    60
actcgctga                                                            69

<210> SEQ ID NO 114
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gggaggacga tgcgggtgac gtggacggcg acagcccagc ataagccacg tgtgacagac    60
gactcgctga                                                           70

<210> SEQ ID NO 115
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
```

```
gggaggacga tgcgggtgac gtggacggcg acagcccagc ataagccacg tgtgacagac    60
gactcgctga                                                          70

<210> SEQ ID NO 116
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gggugacgug gacggcgaca gcccagcaua agccacgugu gac                     43

<210> SEQ ID NO 117
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gggtgacgtg gacggcgaca gcccagcata agccacgtgt gac                     43
```

APTAMERS TO GLYCOPROTEIN VI

This invention was made with government support under Grant No. HL065222 awarded by the National Institutes of Health. The government has certain rights in the invention.

This application is the U.S. national phase of International Application No. PCT/US2011/001750 filed Oct. 13, 2011 which designated the U.S. and claims priority to U.S. Provisional Application No. 61/344,804, filed Oct. 13, 2010, the entire contents of each of which are incorporated herein by reference.

TECHNICAL FIELD

The present invention relates, in general, to glycoprotein VI (GPVI) and, in particular, to aptamers to GPVI and to compositions comprising same. The invention also relates to methods of inhibiting platelet aggregation using aptamers that bind to and inhibit the activity of GPVI. The invention further relates to antidotes to GPVI aptamers and to methods of using such antidotes to reverse aptamer-induced platelet inhibition. The invention also relates to aptamers that bind to and enhance the activity of GPVI.

BACKGROUND

Ribonucleic acid ligands, or aptamers, are a class of drug compounds ideally suited to anticoagulation therapy. They bind to their targets with high affinity and specificity, are only slightly immunogenic and their bioavailability can be tailored to suit a particular clinical need (Nimjee et al, Annu. Rev. Med. 56:555-583(2005)). More recently, research has shown that these drugs can be controlled with antidotes both in vitro and in vivo (Nimjee et al, Molecular Therapy: the Journal of the American Society of Gene Therapy (2006), Mol. Ther. 14:408-45 Epub Jun. 9, 2006, Rusconi et al, Nat. Biotechnol. 22:1423-1428 (2004), Rusconi et al, Nature 419:90-94 (2002)).

Millions of Americans received antiplatelet agents to prevent pathological clot formation (thrombosis). However, these compounds carry a risk of increased bleeding and have no antidote to rapidly reverse activity. Recent studies with antibodies have indicated that blocking GPVI function may protect individuals from thrombosis without an increased risk of bleeding.

The present invention results, at least in part, from studies designed to identify aptamers that bind to GPVI and modulate (inhibit or enhance) its function and/or activity. Aptamers that inhibit GPVI function/activity can be used, for example, therapeutically to inhibit platelet aggregation. Aptamers that enhance GPVI function/activity can be used, for example, to activate platelets; such aptamers can be used in studies designed elucidate the mechanism of GPVI receptor activation.

SUMMARY OF THE INVENTION

In general, the present invention relates to GPVI. More specifically, the invention relates to aptamers to GPVI and to compositions comprising such aptamers. The invention also relates to methods of inhibiting platelet aggregation using aptamers that binds to and inhibit the activity of GPVI. The invention further relates to antidotes to GPVI aptamers and to methods of using such antidotes to reverse aptamer-induced platelet inhibition. The invention also relates to aptamers that bind to and enhance the activity of GPVI.

Objects and advantages of the present invention will be clear from the description that follows.

BRIEF DESCRIPTION OF THE DRAWINGS

FIGS. 1A-1D. Nitrocellulose binding of selected GPVI aptamers. FIGS. 1A-1C. RNA aptamer binding to soluble GPVI. FIG. 1D GPVI aptamers isolated (SEQ ID NOs:4, 7, 11-13, 33, 34 and 45, respectively)

FIG. 5. RNA sequences that bind to human GPVI (SEQ ID NOs:1-45, respectively).

DETAILED DESCRIPTION OF THE INVENTION

Figure 1A:
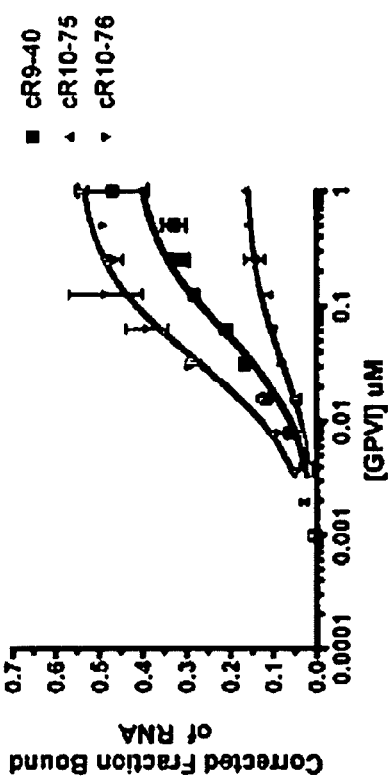

The present invention relates, in one embodiment, to antiplatelet aptamers (DNA or RNA) and to methods of using same in the treatment of, for example, cardiovascular disease. In a specific aspect of this embodiment, the invention relates to RNA aptamers that can bind to and inhibit the activity of GPVI, a platelet membrane protein that participates in platelet adhesion and aggregation. The invention also relates to antidote molecules that can bind to and reverse aptamer-induced platelet inhibition. The antiplatelet agent/antidote pairs of the present invention provide physicians with enhanced control over antithrombotic therapy.

In another embodiment, the invention relates to aptamers that bind to GPVI and enhance its function and/or activity. Aptamers that enhance GPVI function/activity can be used, for example, to activate platelets. More specifically, such aptamers can be used in studies designed elucidate the mechanism of GPVI receptor activation.

Aptamers suitable for use as antiplatelet compounds (e.g., via their ability to bind to and inhibit the activity of GPVI) and aptamers that bind to and enhance activity of GPVI can be prepared using SELEX methodology (see, for example, U.S. Pat. Nos. 5,270,163, 5,817,785, 5,595,887, 5,496,938, 5,475, 096, 5,861,254, 5,958,691, 5,962,219, 6,013,443, 6,030,776, 6,083,696, 6,110,900, 6,127,119, 6,147,204, U.S. Appln 20030175703 and 20030083294, Potti et al, Expert Opin. Biol. Ther. 4:1641-1647 (2004), Nimjee et al, Annu. Rev. Med. 56:555-83 (2005)). The SELEX process consists of iterative rounds of affinity purification and amplification of oligonucleotides from combinatorial libraries to yield high affinity and high specificity ligands. Combinatorial libraries employed in SELEX can be front-loaded with 2'modified RNA nucleotides (e.g., 2'fluoro-pyrimidines) such that the aptamers generated are highly resistant to nuclease-mediated degradation and amenable to immediate activity screening in cell culture or bodily fluids.

Specific aptamers of the invention are described in the Example that follows.

Aptamers of the invention that inhibit the activity of GPVI can be used in the treatment of a cardiovascular disease in humans and non-human animals. For example, these aptamers can be used in patients undergoing percutaneous coronary intervention (PCI) and can be used in the treatment of acute coronary syndromes (ACS) (including stroke and arterial thrombosis). Use of the instant aptamers is expected to significantly reduce the morbidity and mortality associated with thrombosis.

The present invention also relates to antidotes for the antiplatelet aptamers described herein. These antidotes can comprise oligonucleotides that are reverse complements of segments of the antiplatelet aptamers. In accordance with the invention, the antidote is contacted with the targeted aptamer under conditions such that it binds to the aptamer and modifies the interaction between the aptamer and its target molecule (GPVI). Modification of that interaction can result from modification of the aptamer structure as a result of binding by the antidote. The antidote can bind free aptamer and/or aptamer bound to its target molecule.

Antidotes of the invention can be designed so as to bind any particular aptamer with a high degree of specificity and a desired degree of affinity. The antidote can be designed so that, upon binding to the targeted aptamer, the three-dimensional structure of that aptamer is altered such that the aptamer can no longer bind to its target molecule or binds to its target molecule with less affinity.

Antidotes of the invention include any pharmaceutically acceptable agent that can bind an aptamer and modify the interaction between that aptamer and its target molecule (e.g., by modifying the structure of the aptamer) in a desired manner. Examples of such antidotes include oligonucleotides complementary to at least a portion of the aptamer sequence (including ribozymes or DNAzymes or peptide nucleic acids (PNAs)), nucleic acid binding peptides, polypeptides or proteins (including nucleic acid binding tripeptides (see, generally, Hwang et al, Proc. Natl. Acad. Sci. USA 96:12997 (1999)), and oligosaccharides (e.g., aminoglycosides (see, generally, Davies et al, Chapter 8, p. 185, RNA World, Cold Spring Harbor Laboratory Press, eds Gestlaad and Atkins (1993), Werstuck et al, Science 282:296 (1998), U.S. Pat. Nos. 5,935,776 and 5,534,408). (See also Chase et al, Ann. Rev. Biochem. 56:103 (1986), Eichhorn et al, J. Am. Chem. Soc. 90:7323 (1968), Dale et al, Biochemistry 14:2447 (1975) and Lippard et al, Acc. Chem. Res. 11:211 (1978)).

Standard binding assays can be used to screen for antidotes of the invention (e.g., using BIACORE assays). That is, candidate antidotes can be contacted with the aptamer to be targeted under conditions favoring binding and a determination made as to whether the candidate antidote in fact binds the aptamer. Candidate antidotes that are found to bind the aptamer can then be analyzed in an appropriate bioassay (which will vary depending on the aptamer and its target molecule) to determine if the candidate antidote can affect the binding of the aptamer to its target molecule.

In a preferred embodiment, the antidote of the invention is an oligonucleotide that comprises a sequence complementary to at least a portion of the targeted aptamer sequence. Advantageously, the antidote oligonucleotide comprises a sequence complementary to 6-25 consecutive nucleotides of the targeted aptamer, preferably, 8-20 consecutive nucleotides, more preferably, 10-15 consecutive nucleotides.

Formation of duplexes by binding of complementary pairs of short oligonucleotides is a fairly rapid reaction with second order association rate constants generally between $1 \times 10^6$ and $3 \times 10^6 \, M^{-1} \, s^{-1}$. Thus, the effect on an aptamer by formation of a duplex with a complimentary oligonucleotide is rapid. Stability of short duplexes is highly dependent on the length and base-composition of the duplex. The thermodynamic parameters for formation of short nucleic acid duplexes have been rigorously measured, resulting in nearest-neighbor rules for all possible base pairs such that accurate predictions of the free energy, $T_m$ and thus half-life of a given oligoribonucleotide duplex can be calculated (e.g., Xia et al, Biochem. 37:14719 (1998) (see also Eguchi et al, Antisense RNA, Annu. Rev. Biochem. 60:631 (1991)).

Antidote oligonucleotides of the invention can comprise modified nucleotides that confer improved characteristics, such as improved in vivo stability and/or improved delivery characteristics. Examples of such modifications include chemical substitutions at the sugar and/or backbone and/or base positions. Oligonucleotide antidotes can contain nucleotide derivatives modified at the 5- and 2' positions of pyrimidines, for example, nucleotides can be modified with 2'amino, 2'-fluoro and/or 2'-O-methyl. Modifications of the antidote oligonucleotides of the invention can include those that provide other chemical groups that incorporate additional charge, polarization, hydrophobicity, hydrogen bonding and/or electrostatic interaction. Such modifications include but are not limited to, 2' position sugar modifications, locked nucleic acids, 5 position pyrimidine modifications, 8 position purine modifications, modification at exocyclic amines, substitution of 4-thiouridine, substitution of 5-bromo or 5-iodo-uracil, backbone modifications, phosphorothioate or alkyl phosphate modifications, methylations, unusual base-pairing combinations such as isobases isocytidine and isoguanidine, etc. Modifications can also include 3' and 5' modifications, such as capping, and addition of PEG or cholesterol. (See also Manoharan, Biochem. Biophys. Acta 1489: 117 (1999); Herdewijn, Antisense Nucleic Acid Drug Development 10:297 (2000); Maier et al, Organic Letters 2:1819 (2000)).

A typical aptamer possesses some amount of secondary structure—its active tertiary structure is dependent on formation of the appropriate stable secondary structure. Therefore, while the mechanism of formation of a duplex between a complementary oligonucleotide antidote of the invention and an aptamer is the same as between two short linear oligoribonucleotides, both the rules for designing such interactions and the kinetics of formation of such a product are impacted by the intramolecular aptamer structure. The rate of nucleation is important for formation of the final stable duplex, and the rate of this step is greatly enhanced by targeting the oligonucleotide antidote to single-stranded loops and/or single-stranded 3' or 5' tails present in the aptamer. For the formation of the intermolecular duplex to occur, the free energy of formation of the intermolecular duplex has to be favorable with respect to formation of the existing intramolecuar duplexes within the targeted aptamer. Thus, oligonucleotide antidotes of the invention are advantageously targeted at single-stranded regions of the aptamer. This facilitates nucleation and, therefore, the rate of aptamer activity modulation, and also, generally leads to intermolecular duplexes that contain more base pairs than the targeted aptamer.

Various strategies can be used to determine the optimal site for oligonucleotide binding to a targeted aptamer. An empirical strategy can be used in which complimentary oligonucleotides are "walked" around the aptamer. In accordance with this approach, 2'Omethyl oligonucleotides (e.g., 2'Omethyl oligonucleotides) about 15 nucleotides in length can be used that are staggered by about 5 nucleotides on the aptamer. An empirical strategy may be particularly effective because the impact of the tertiary structure of the aptamer on the efficiency of hybridization can be difficult to predict. Assays described, for example, in U.S. Appln. No. 20030083294 can be used to assess the ability of the different oligonucleotides to hybridize to a specific aptamer, with particular emphasis on the molar excess of the oligonucleotide required to achieve complete binding of the aptamer. The ability of the different oligonucleotide antidotes to increase the rate of dissociation of the aptamer from its target molecule can also be determined by conducting standard kinetic studies using, for example, BIACORE assays. Oligonucleotide antidotes can be selected such that a 5-50 fold molar excess of oligonucleotide, or less, is required to modify the interaction between the aptamer and its target molecule in the desired manner.

Alternatively, the targeted aptamer can be modified so as to include a single-stranded tail (3' or 5') in order to promote association with an oligonucleotide modulator. Suitable tails can comprise 1 to 20 nucleotides, preferably, 1-10 nucleotides, more preferably, 1-5 nucleotides and, most preferably, 3-5 nucleotides (e.g., modified nucleotides such as 2'Omethyl sequences). Tailed aptamers can be tested in binding and bioassays (e.g., as described in U.S. Appln. No. 20030083294) to verify that addition of the single-stranded tail does not disrupt the active structure of the aptamer. A series of oligonucleotides (for example, 2'Omethyl oligonucleotides) that can form, for example, 1, 3 or 5 basepairs with the tail sequence can be designed and tested for their ability to associate with the tailed aptamer alone, as well as their ability to increase the rate of dissociation of the aptamer from its target molecule.

In addition to antidote oligonucleotides described above, the invention also relates to the use of antidotes that bind target aptamers in a sequence independent manner. Such antidotes are described in detail in U.S. application Ser. No. 12/588,016 (see also Oney et al, Nat Med. 15(10):1224-8 (2009). Epub 2009 Oct. 4.)

The present invention relates to antidotes that specifically and rapidly reverse the anticoagulant and antithrombotic effects of aptamers that target and inhibit GPVI activity. In accordance with this embodiment, antidotes (advantageously, oligonucleotide inhibitors) are administered that reverse the aptamer activity. At least three clinical scenarios exist in which the ability to rapidly reverse the activity of an aptamer of the invention that inhibits GPVI function is desirable. The first case is when anticoagulant or antithrombotic treatment leads to hemorrhage. The potential for morbidity or mortality from this type of bleeding event can be a significant risk. The second case is when emergency surgery is required for patients who have received antithrombotic treatment. This clinical situation can arise, for example, in patients who require emergency coronary artery bypass grafts while undergoing PCI under the coverage of GPVI inhibitors. The third case is when an anticoagulant aptamer is used during a cardiopulmonary bypass procedure. Bypass patients are predisposed to post operative bleeding. In each case, acute reversal of the anticoagulant effects of an aptamer via an antidote (e.g., an oligonucleotide antidote targeted to an anticoagulant or antithrombotic aptamer) allows for improved, and likely safer, medical control of the anticoagulant or antithrombotic compound.

The antiplatelet aptamers and antidotes of the invention can be formulated into pharmaceutical compositions that can include, in addition to the aptamer or antidote, a pharmaceutically acceptable carrier, diluent or excipient. The precise nature of the composition will depend, at least in part, on the nature of the aptamer or antidote and the route of administration. Optimum dosing regimens can be readily established by one skilled in the art and can vary with the aptamer and antidote, the patient and the effect sought. Because the antidote activity is durable, once the desired level of modulation of the aptamer by the antidote is achieved, infusion of the antidote can be terminated, allowing residual antidote to clear the human or non-human animal. This allows for subsequent re-treatment of the human or animal with the aptamer as needed. Alternatively, and in view of the specificity of antidote oligonucleotides of the invention, subsequent treatment can involve the use of a second, different aptamer/antidote oligonucleotide pair.

The antiplatelet aptamers and antidotes can be administered directly (e.g., alone or in a liposomal formulation or complexed to a carrier (e.g., PEG)) (see for example, U.S. Pat. No. 6,147,204 for examples of lipophilic compounds and non-immunogenic high molecular weight compounds suitable for formulation use). Alternatively, oligonucleotide antidotes of the invention can be produced in vivo following administration of a construct comprising a sequence encoding the oligonucleotide. Techniques available for effecting intracellular delivery of RNA antidotes of gene expression can be used (see generally Sullenger et al, Mol. Cell Biol. 10:6512 (1990)). (Also incorporated by reference is the following citation that describes APTT and other clotting assays: Quinn et al, J. Clin. Lab. Sci. 13(4):229-238 (2000). This review describes the properties and biochemistry of various clotting assays including APTT, PT and thrombin time assays, and their use in diagnosing coagulopathies.)

In addition to the antiplatelet aptamers described above, the present invention also relates to aptamers that bind to GPVI and enhance its function and/or activity. Aptamers that enhance GPVI function/activity can be used, for example, to activate platelets. Aptamers that enhance GPVI function/activity can be used in studies designed elucidate the mechanism of GPVI receptor activation. For example, soluble GPVI protein can be incubated with a platelet-activating GPVI aptamer and the ability of the aptamer to induce aggregation of the soluble receptor determined using, for example, the analytical ultracentrifugation technique of Horii et al (Blood 108:936 (2006)). In accordance with this approach, the stoichiometry of the aptamer/protein complex (or the ratio of aptamer:protein in the complex) can be analyzed to determine if the aptamer is aggregating and forming a multimer, which may bind to several GPVI receptors on the platelet surface and cause receptor clustering, resulting in platelet activation. Alternatively, platelets can be incubated with an activating GPVI aptamer and the ability of the aptamer to induce phosphorylation of proteins that are "downstream" of GPVI determined using, for example, the western blotting methodologies of Asselin et al (Blood 89:1235 (1997)) and Polgar et al (J. Biol. Chem. 272:13576 (1997)). This approach is based on the premise that platelet activation through GPVI leads to a phosphorylation signaling cascade, whereby specific proteins become phosphorylated.

Certain aspects of the invention are described in greater detail in the non-limiting Example that follows. (See also PCT/US2007/022358, PCT/US2008/0014119, U.S. application Ser. No. 12/588,016, U.S. application Ser. No. 12/311,943 and U.S. application Ser. No. 12/588,016.)

EXAMPLE

Figure 1B:
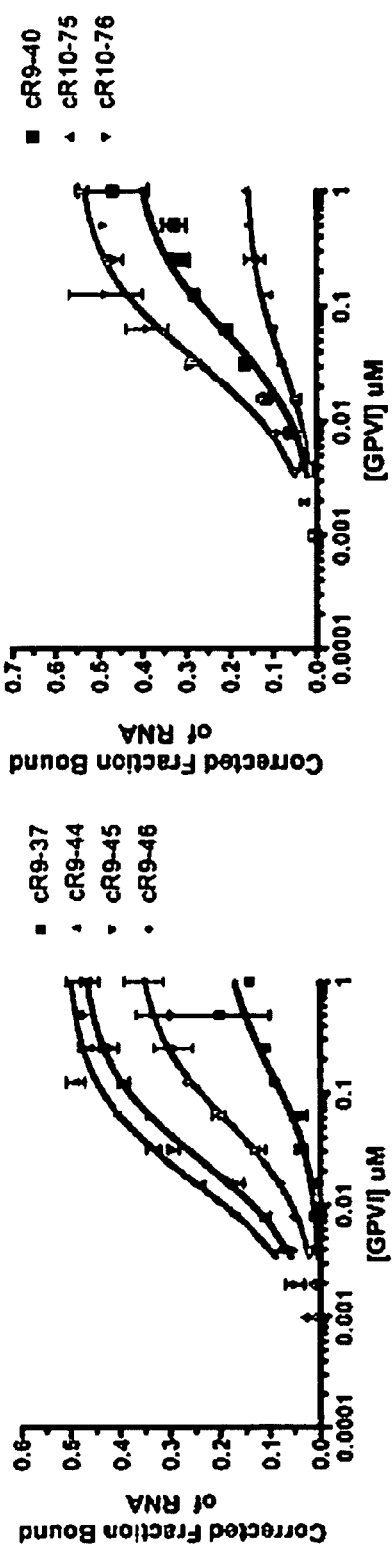
Figure 1C:
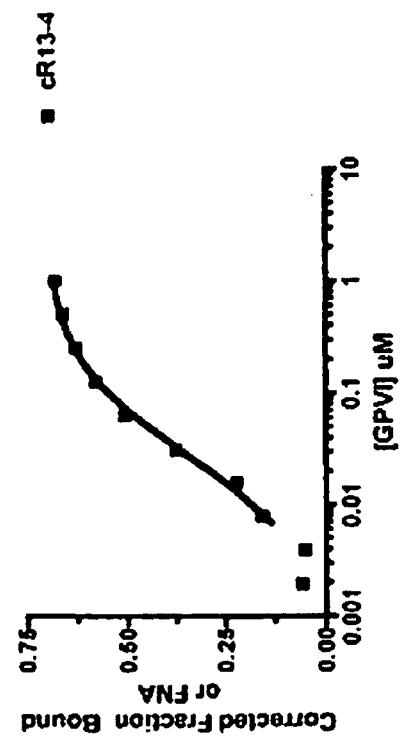

To generate a high affinity aptamer against GPVI, SELEX was performed against the purified extracellular domain of human GPVI using a pool of 2'fluoro-modified RNA sequences. As a result, several aptamer sequences were generated that bind to the protein target with high affinity. As shown in FIG. 1, several RNA sequences were isolated that bind to GPVI with high affinity and have dissociation constants ($K_d$s) of 20-160 nM.

Figure 2:
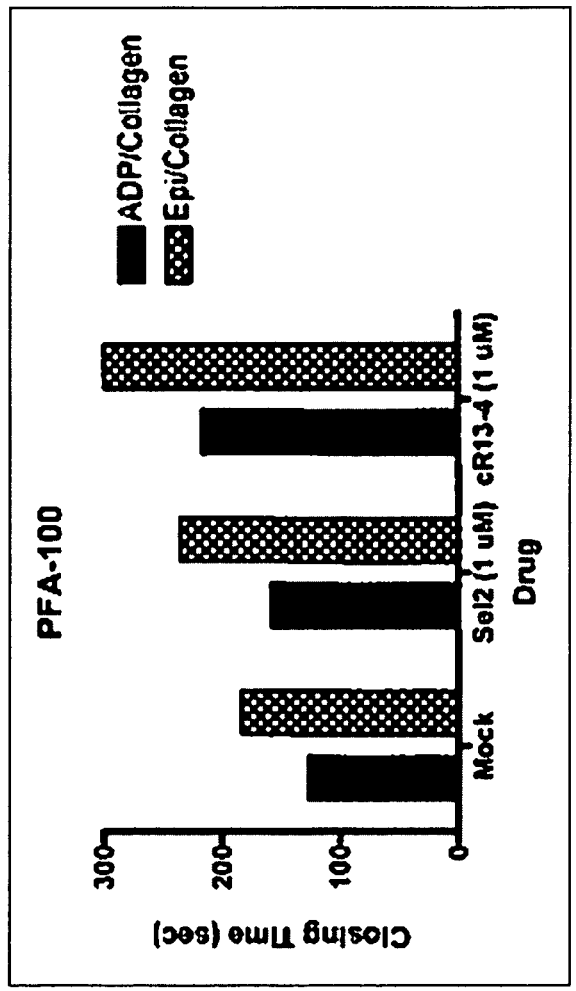
FIG. 2. PFA-100 assay with aptamer cR13-4.

To initially probe the functionality of the clones, a platelet functional analysis assay (PFA-100) was used that measures time until platelet plug formation in vitro. Whole human blood was drawn from human subjects under an approved IRB protocol. Citrated blood was then individually incubated with 1 μM of the aptamers (13-4) or a control RNA (a randomized, starting SELEX library, Se12) and the assay was run according to the manufacturers protocol. As shown in the FIG. 2, aptamer cR13-4 prolongs closing time with both types of PFA-100 cartridges (ADP or epinephrine) compared to the control RNA in a PFA-100 assay.

Figure 3:
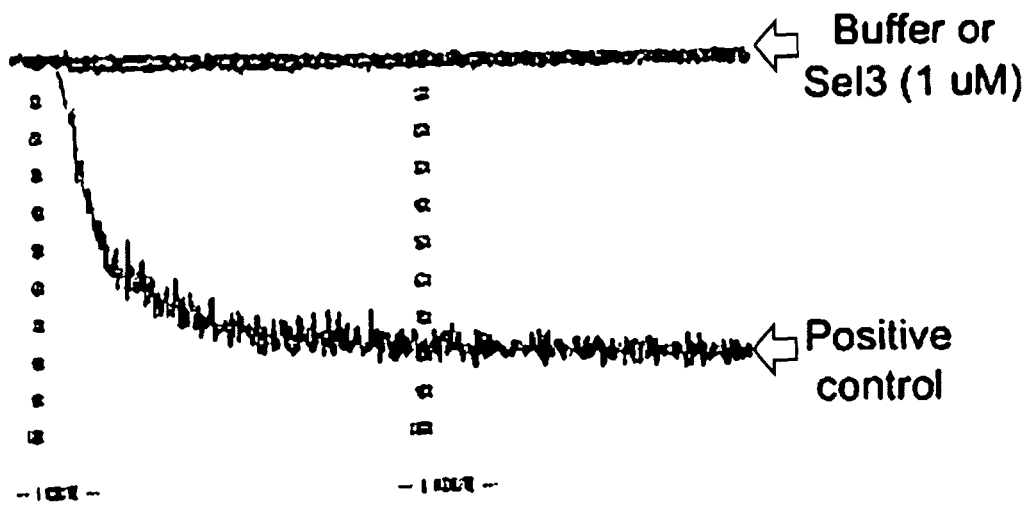
FIG. 3. Platelet aggregometry with aptamer cR13-4.
Figure 3:
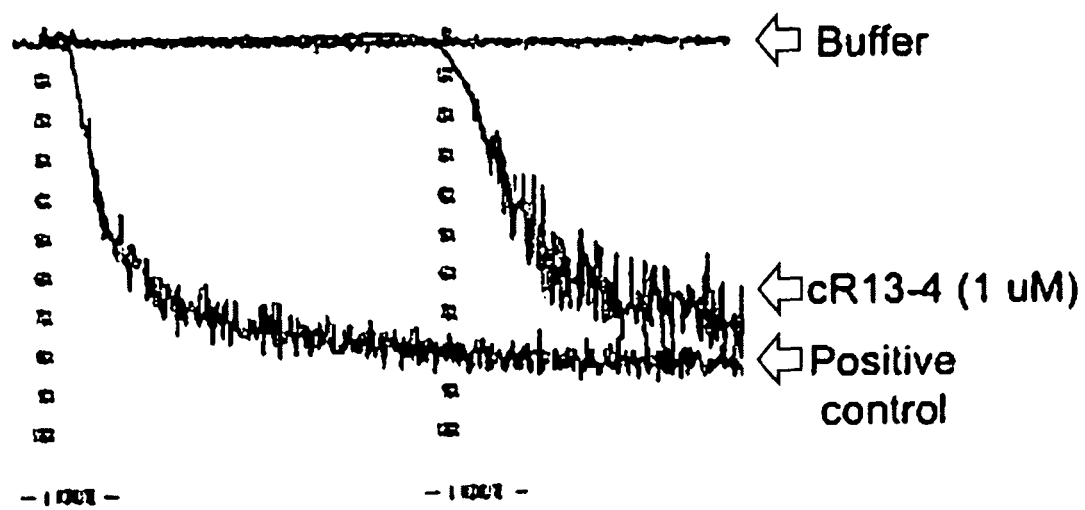
Figure 4:
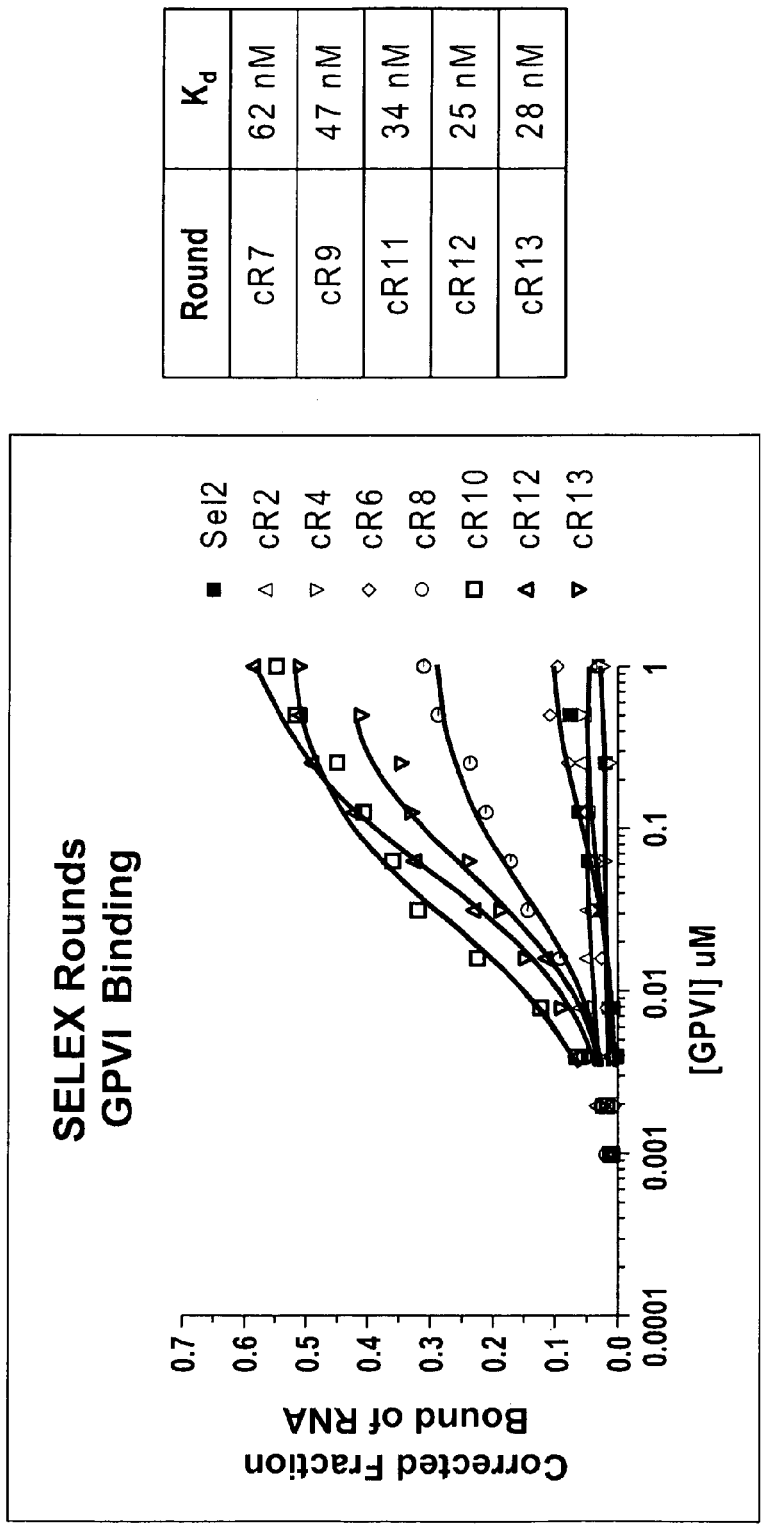
FIG. 4. GPVI aptamer data.
Figure 4:
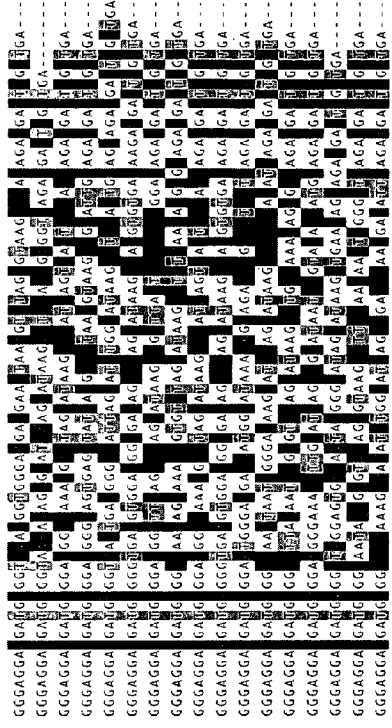
Figure 4:
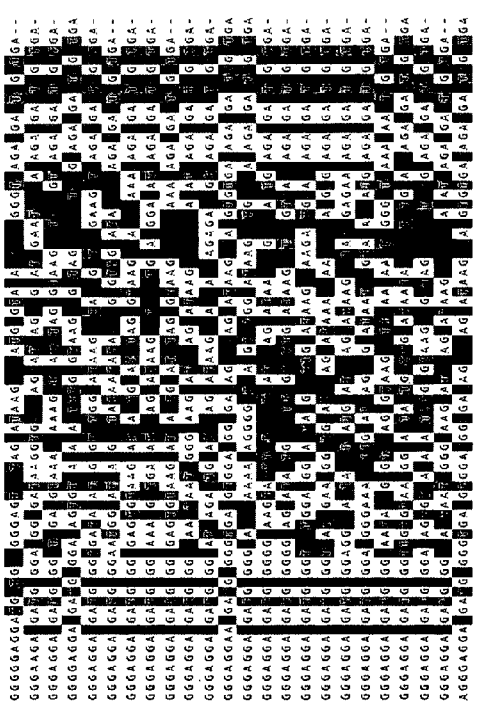
Figure 4:
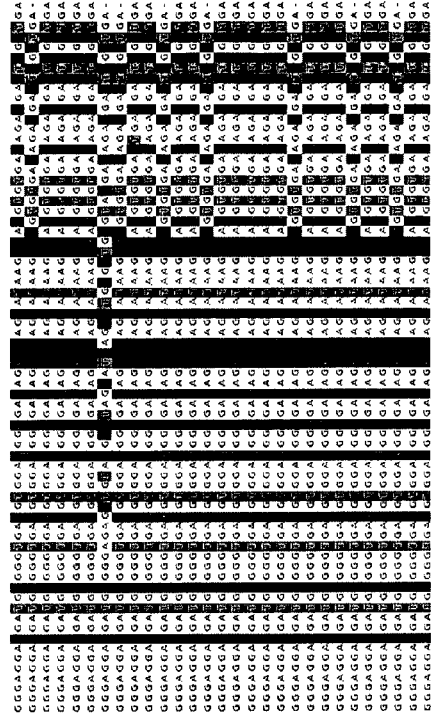
Figure 4:
Figure 4:
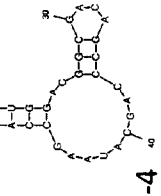
Figure 4:
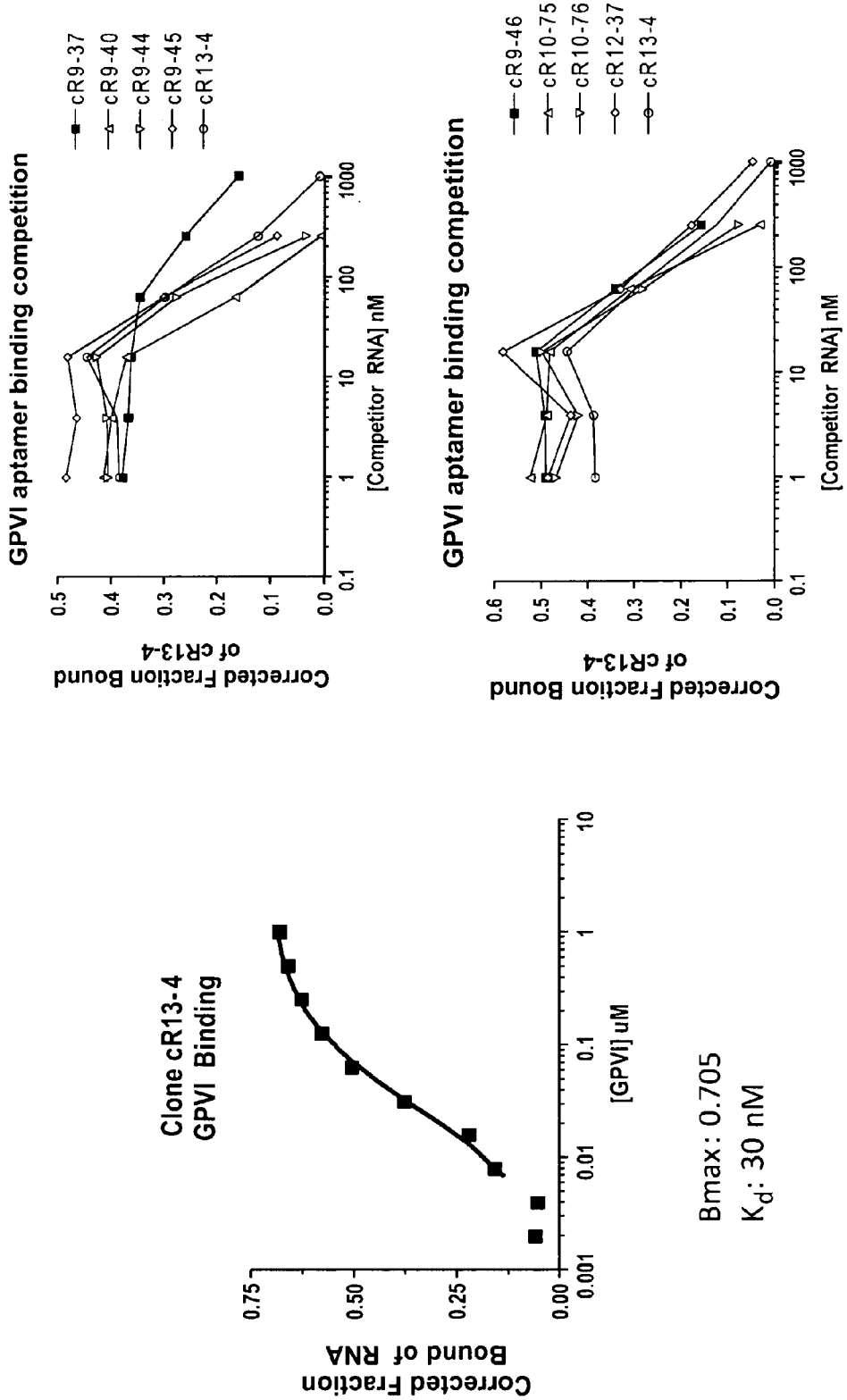
Figure 4:
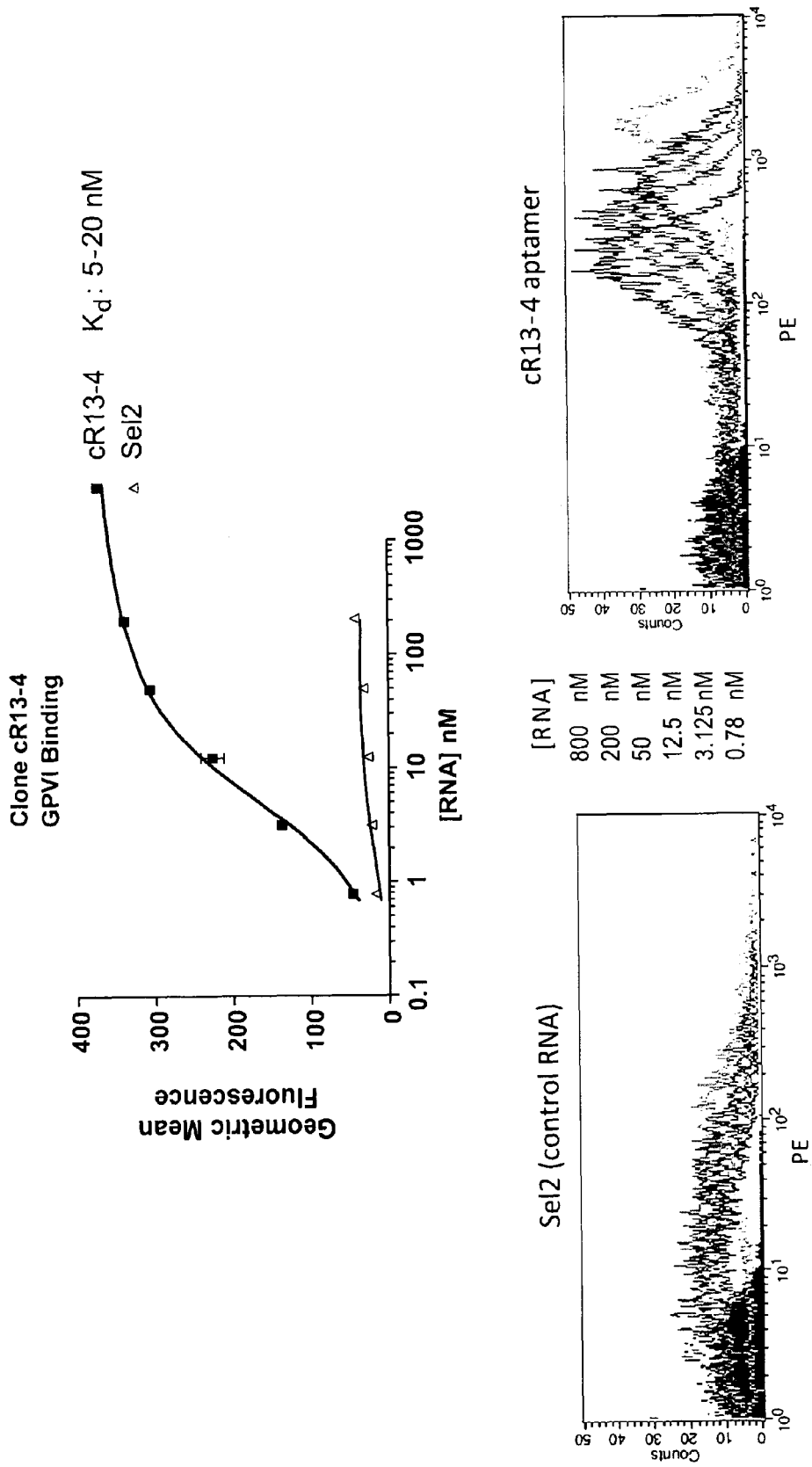
Figure 4:
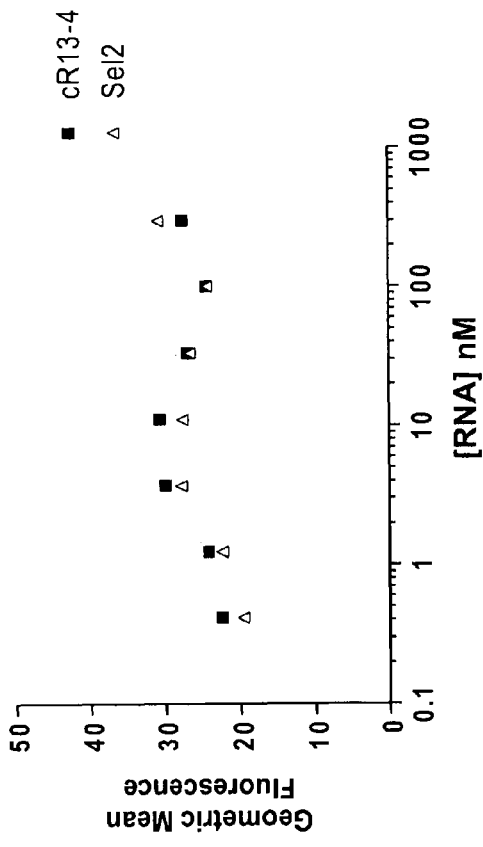
Figure 4:
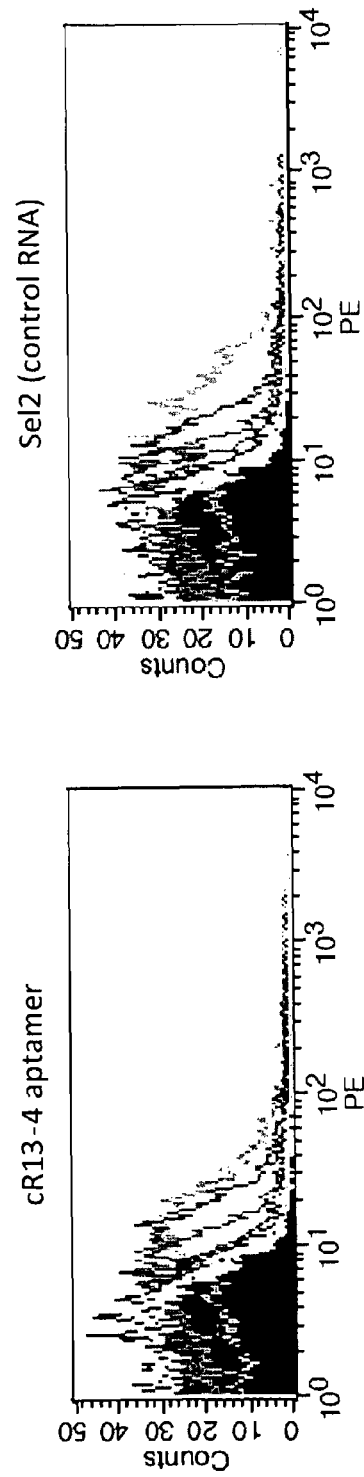
Figure 4:
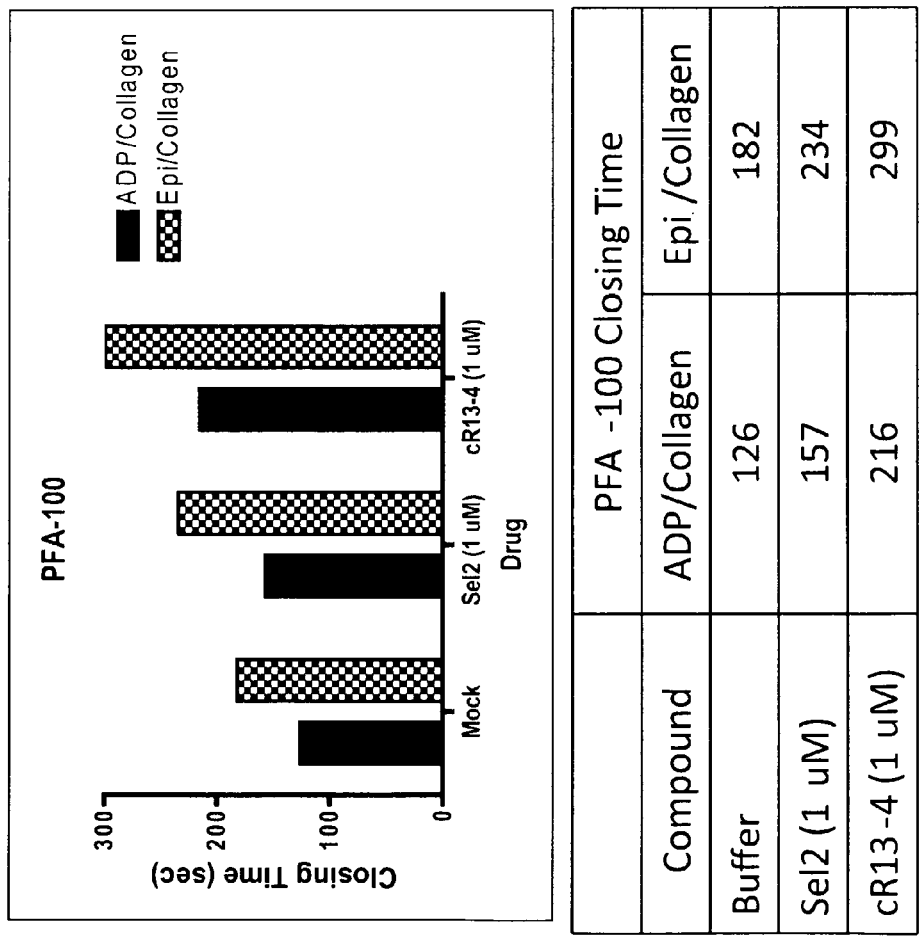
Figure 4:
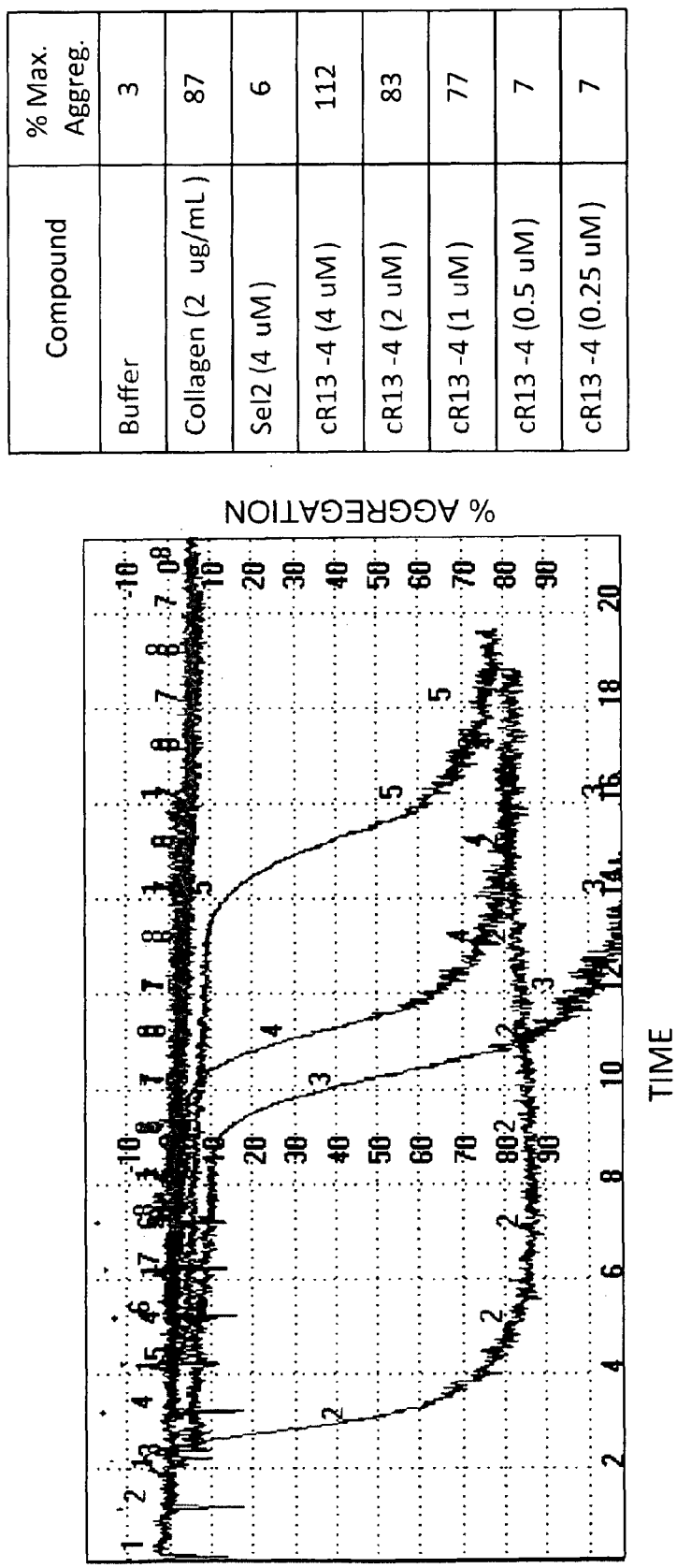
Figure 4:
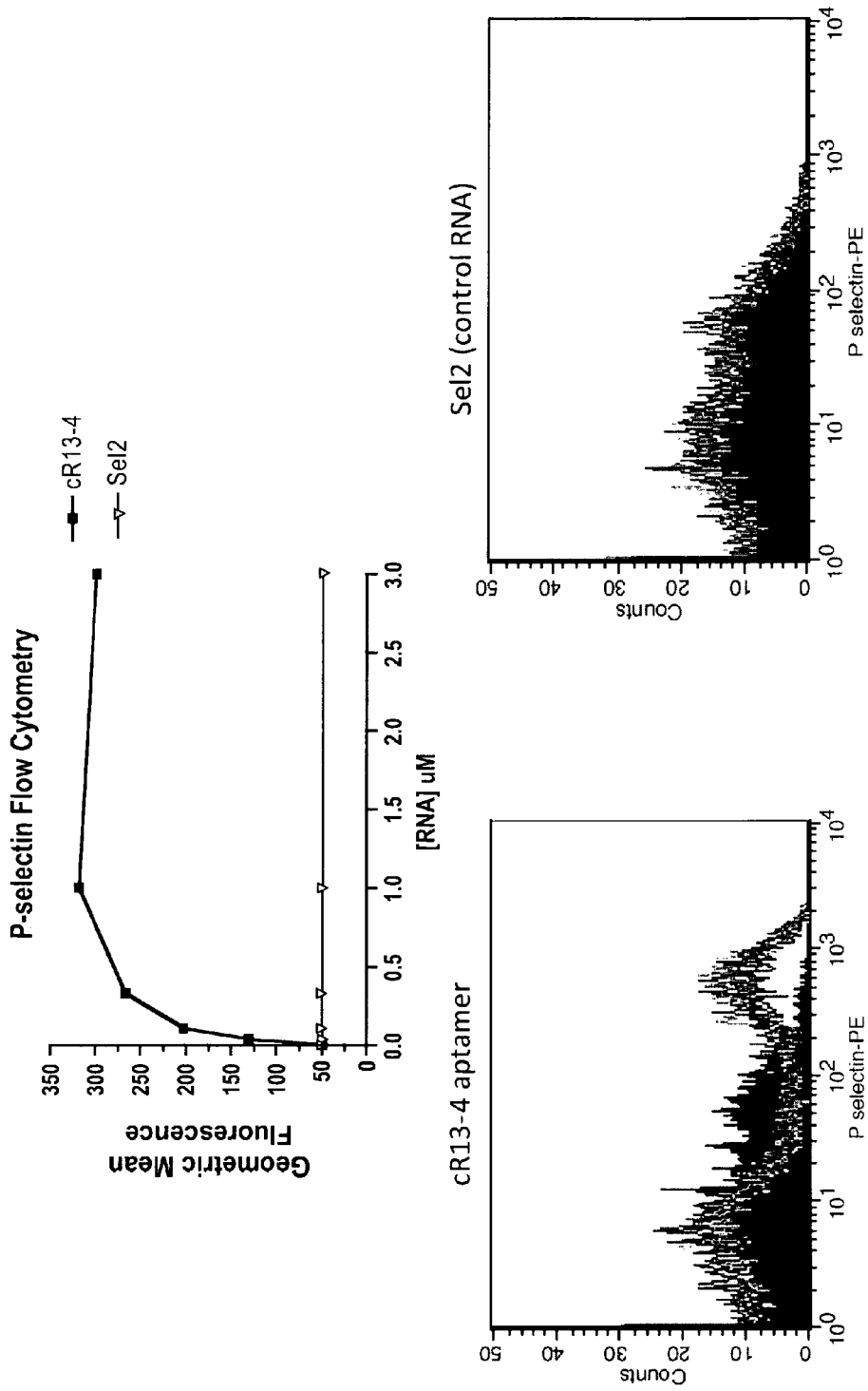
Figure 4:
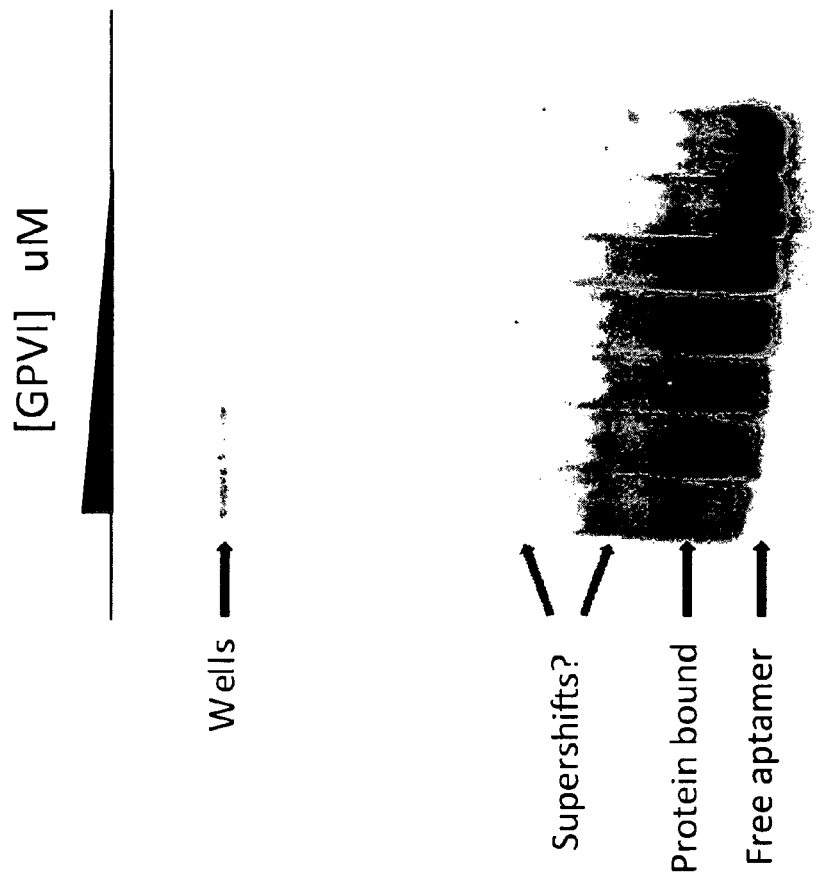
Figure 4:
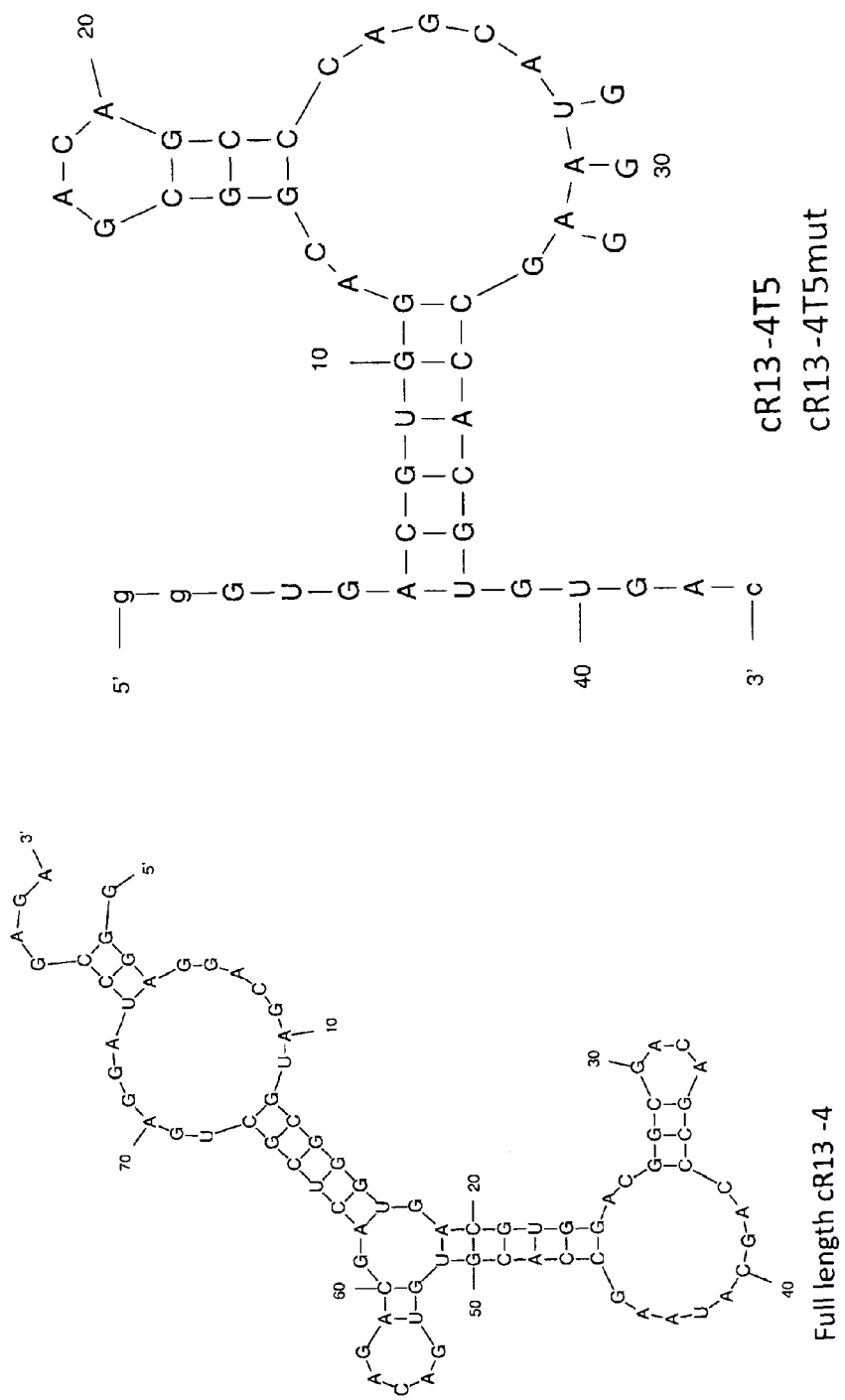
Figure 4:
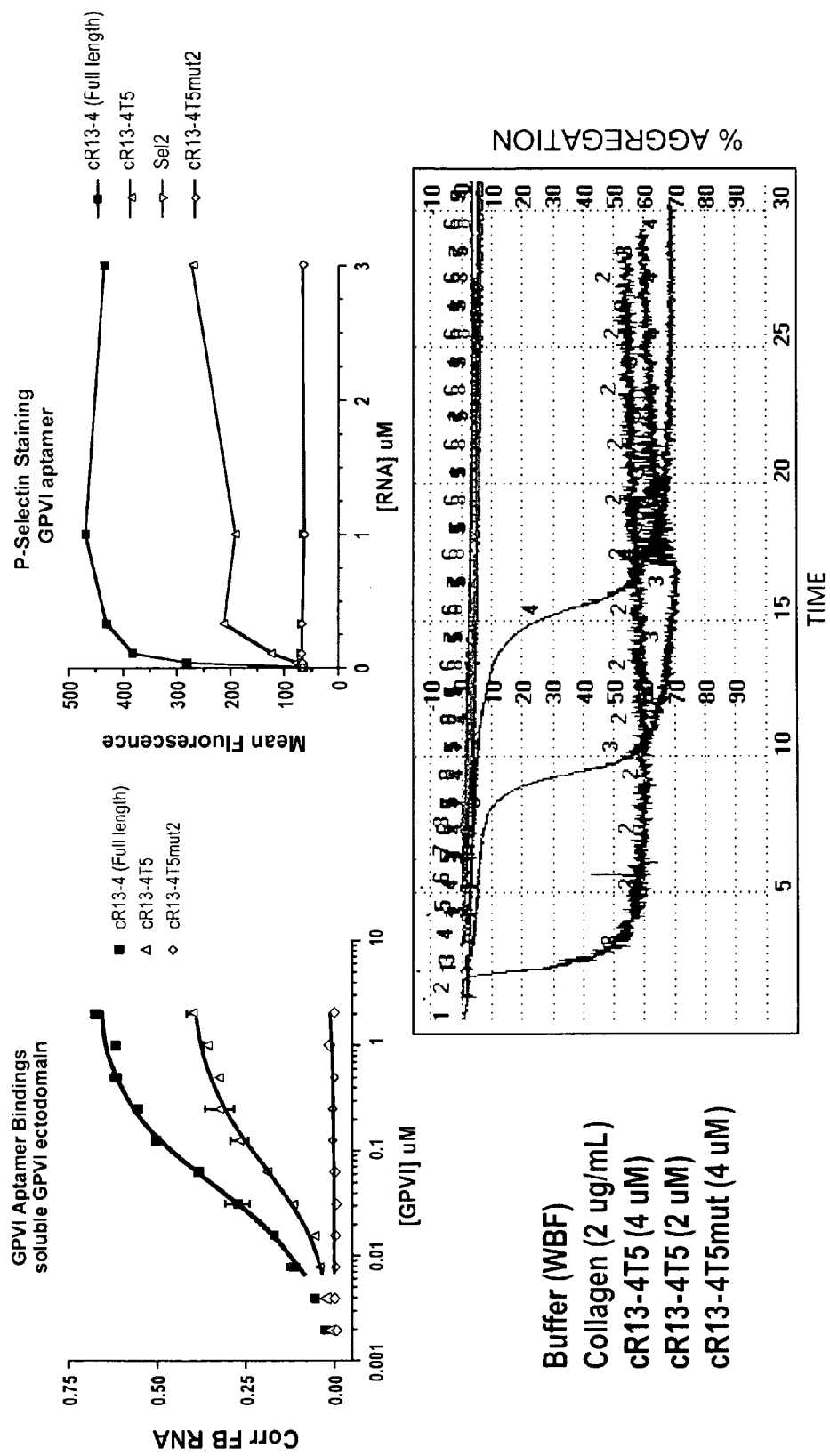
Figure 4:
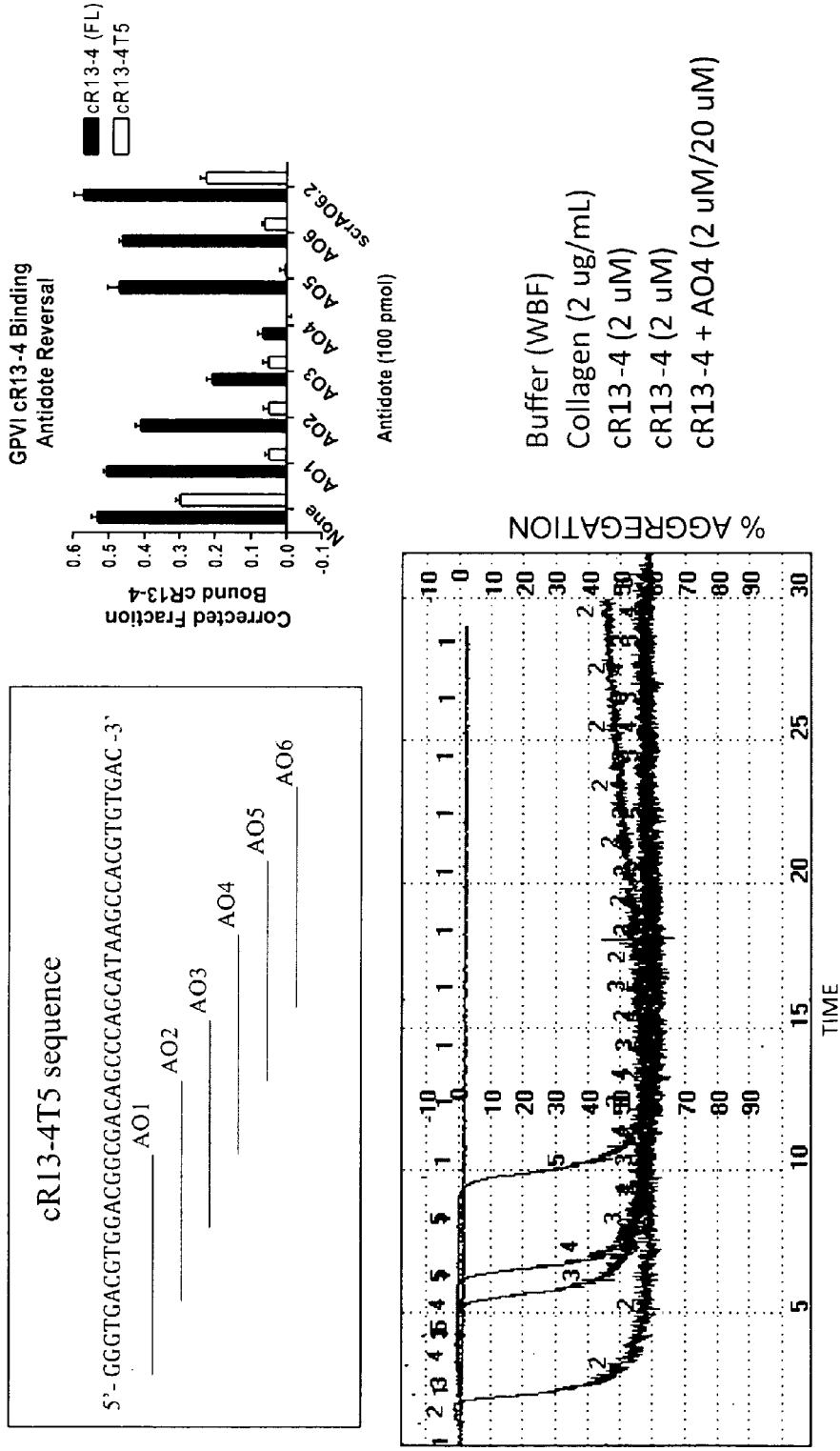

Additionally, the functionality of the isolated RNA aptamers was probed by testing them in platelet aggregometry, which quantifies platelet aggregation in platelet rich plasma (PRP) via light transmission of the sample. Whole human blood was drawn from human subjects under an approved IRB protocol. Citrated blood was spun to obtain PRP, and then individually incubated with 1 µM of the aptamer (cR13-4) or the Sel2 control RNA. As shown in FIG. 3, aptamer cR13-4 stimulates platelets and causes them to aggregate compared to the control RNA. (See also FIGS. 4 and 5.)

The discovery of the GPVI aptamers is important because it demonstrates that the technology can be translated into antiplatelet therapeutics. Although inhibitory aptamers to other platelet proteins have been generated (e.g., to Von Willebrand factor, platelet glycoprotein IIb-3a), inhibition of these platelet proteins can cause excessive bleeding. Aptamers that block GPVI can represent a safer antiplatelet alternative. Such aptamers can be identified using the platelet aggregometry techniques described above (see also, for example, Nieswandt et al, J. Biol. Chem. 275:23998 (2000) and Lecut et al, J. Thromb. Haemost. 1(12):2653-62 (2003)).

All documents and other information sources cited above are hereby incorporated in their entirety by reference.

---

What is claimed is:

1. An aptamer that binds to and inhibits the activity of GPVI, wherein the aptamer comprises SEQ ID NO: 116.

2. A method of treating thrombosis in a human or non-human subject in need thereof comprising administering to said subject an amount of said aptamer according to claim 1 sufficient to effect said treatment.

3. The method according to claim 2 wherein said subject is undergoing percutaneous coronary intervention.

4. The method according to claim 2 wherein said subject suffers from an acute coronary syndrome.

5. A composition comprising the aptamer according to claim 1 and a carrier.

6. The aptamer of claim 1, wherein the aptamer is selected from the group consisting of SEQ ID NO: 116, SEQ ID NO: 24, SEQ ID NO: 30, SEQ ID NO: 34, SEQ ID NO: 42 and SEQ ID NO: 45.

7. The aptamer of claim 6, further comprising a carrier.

8. The aptamer of claim 1, further comprising a modified nucleotide.

9. The aptamer of claim 8, wherein the modified nucleotide is a 2' O-methyl nucleotide.

10. The aptamer of claim 6, further comprising a modified nucleotide.

11. The aptamer of claim 10, wherein the modified nucleotide is a 2' O-methyl nucleotide.

12. A method of inhibiting platelet aggregation in a human or non-human subject in need thereof comprising administering to said subject an amount of said aptamer according to claim 1 sufficient to effect said treatment.

13. A method of treating thrombosis in a human or non-human subject in need thereof comprising administering to said subject an amount of said aptamer according to claim 6 sufficient to effect said treatment.

14. The method according to claim 13 wherein said subject is undergoing percutaneous coronary intervention.

15. The method according to claim 13 wherein said subject suffers from an acute coronary syndrome.

16. A method of inhibiting platelet aggregation in a human or non-human subject in need thereof comprising administering to said subject an amount of said aptamer according to claim 6 sufficient to effect said treatment.

* * * * *